(12) United States Patent
Hui et al.

(10) Patent No.: US 7,198,625 B1
(45) Date of Patent: Apr. 3, 2007

(54) SURGICAL INSTRUMENT WITH RETRACTABLE SHEATH

(75) Inventors: Simon S. Hui, San Jose, CA (US); Reid S. Cover, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 231 days.

(21) Appl. No.: 10/859,765

(22) Filed: Jun. 2, 2004

Related U.S. Application Data

(60) Provisional application No. 60/508,167, filed on Oct. 1, 2003.

(51) Int. Cl.
*A61B 18/14* (2006.01)
(52) U.S. Cl. ...................................................... 606/41
(58) Field of Classification Search .................. 606/41
See application file for complete search history.

(56) References Cited

U.S. PATENT DOCUMENTS

| | | | | |
|---|---|---|---|---|
| 4,776,346 A * | 10/1988 | Beraha et al. | ............... | 600/567 |
| 4,836,201 A * | 6/1989 | Patton et al. | ................ | 606/107 |
| 4,900,311 A * | 2/1990 | Stern et al. | .................. | 604/198 |
| 4,907,599 A * | 3/1990 | Taylor | ......................... | 600/567 |
| 4,919,129 A | 4/1990 | Weber, Jr. et al. | | |
| 5,066,295 A * | 11/1991 | Kozak et al. | .................. | 606/47 |
| 5,104,382 A * | 4/1992 | Brinkerhoff et al. | ... | 604/164.12 |
| 5,125,413 A * | 6/1992 | Baran | ......................... | 600/567 |
| 5,133,713 A * | 7/1992 | Huang et al. | .................. | 606/46 |
| 5,195,959 A | 3/1993 | Smith | | |
| 5,197,963 A * | 3/1993 | Parins | ......................... | 606/46 |
| 5,312,400 A * | 5/1994 | Bales et al. | .................... | 606/41 |
| 5,350,356 A * | 9/1994 | Bales et al. | .................... | 604/27 |
| 5,380,321 A * | 1/1995 | Yoon | ............................ | 606/41 |
| 5,391,177 A * | 2/1995 | Schwartz | ..................... | 606/167 |
| 5,425,718 A * | 6/1995 | Tay et al. | ............. | 604/164.11 |
| 5,458,597 A * | 10/1995 | Edwards et al. | ............. | 606/41 |
| 5,472,441 A * | 12/1995 | Edwards et al. | ............. | 606/41 |
| 5,556,376 A * | 9/1996 | Yoon | ........................... | 604/15 |
| 5,609,573 A * | 3/1997 | Sandock | ....................... | 604/22 |
| 5,665,102 A * | 9/1997 | Yoon | .......................... | 606/185 |
| 6,293,945 B1 * | 9/2001 | Parins et al. | .................. | 606/45 |
| 6,355,034 B2 * | 3/2002 | Cosmescu | ..................... | 606/45 |
| 6,491,690 B1 | 12/2002 | Goble et al. | | |
| 6,613,026 B1 * | 9/2003 | Palasis et al. | ............... | 604/272 |
| 6,899,712 B2 * | 5/2005 | Moutafis et al. | .............. | 606/49 |
| 2003/0004528 A1 * | 1/2003 | Ishikawa | .................... | 606/169 |
| 2004/0087914 A1 * | 5/2004 | Bryan et al. | ................. | 604/264 |

* cited by examiner

*Primary Examiner*—Michael Peffley
*Assistant Examiner*—Alex Toy
(74) *Attorney, Agent, or Firm*—Blakely Sokoloff Taylor & Zafman LLP

(57) ABSTRACT

An electrosurgical suction/irrigation instrument includes a shaft hub, an electrically conductive member, and a sheath. The conductive member has a proximal end mounted to the shaft hub and a distal end including a conductive operating tip. The sheath covers the conductive member so that the operating tip is covered when the sheath is in an extended position and exposed when the sheath is in a retracted position. The sheath hub is coupled to the sheath and is movably engaged with the shaft hub. The surgical instrument further includes a locking mechanism to lock the sheath in the retracted position, and a bias element to bias the sheath toward the extended position.

28 Claims, 31 Drawing Sheets

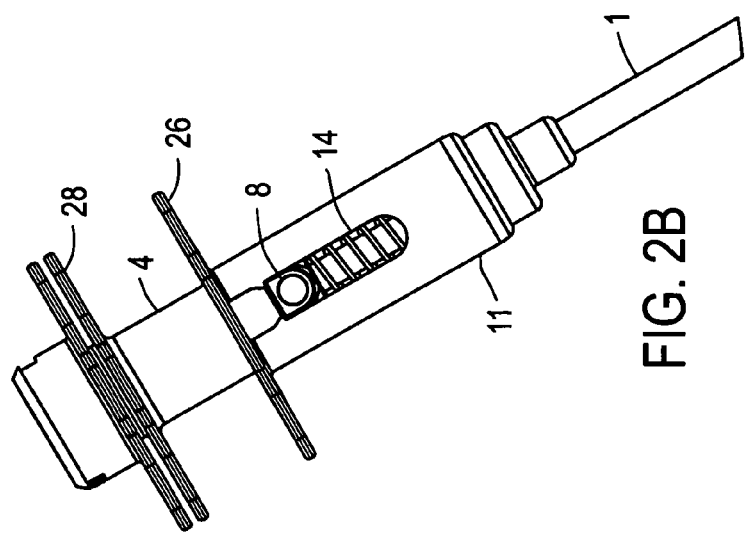
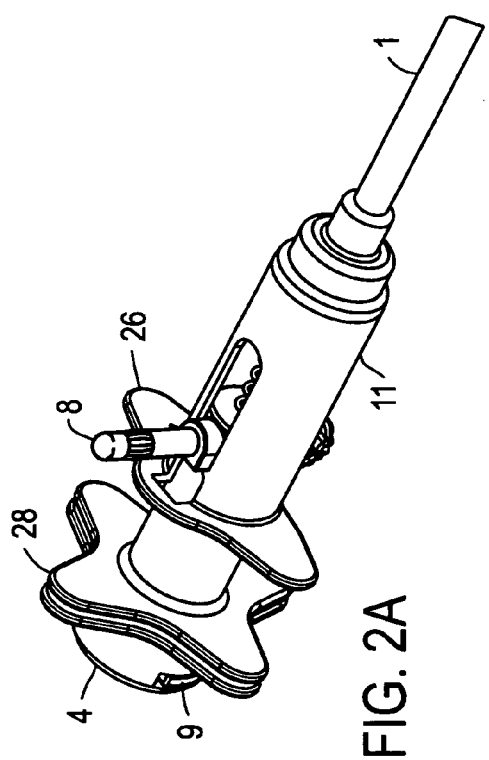
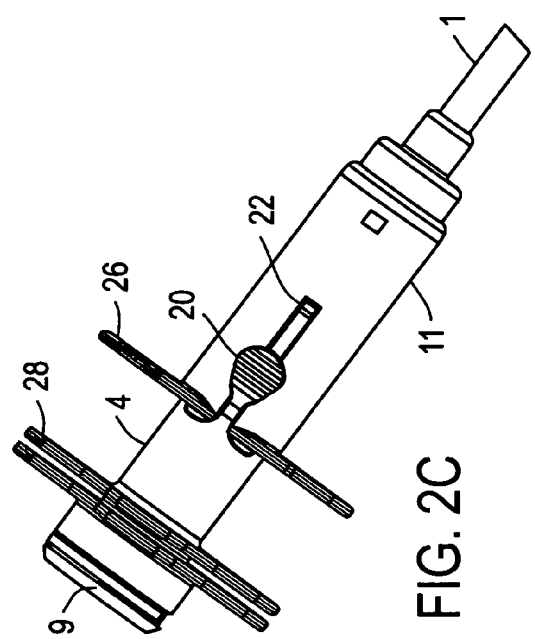

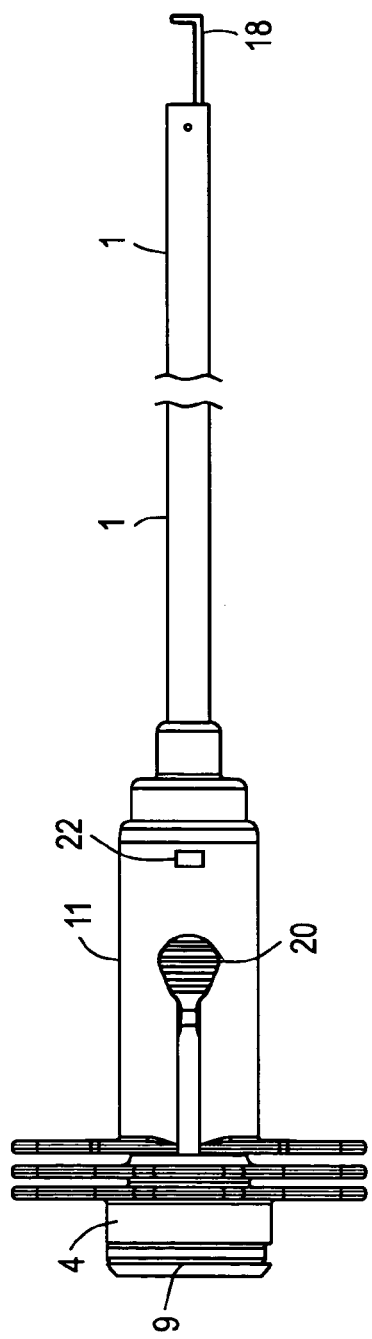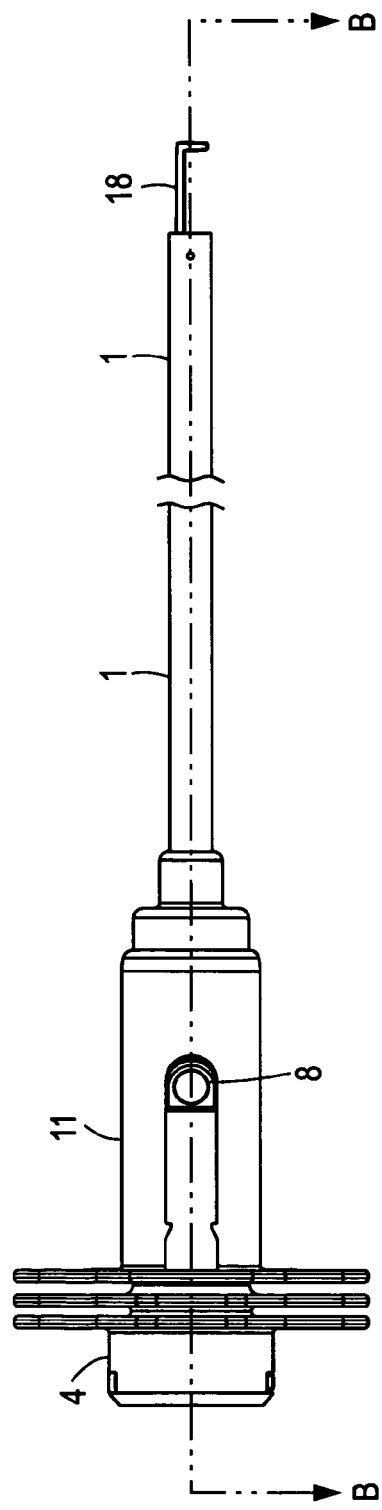
FIG. 3A
FIG. 3B

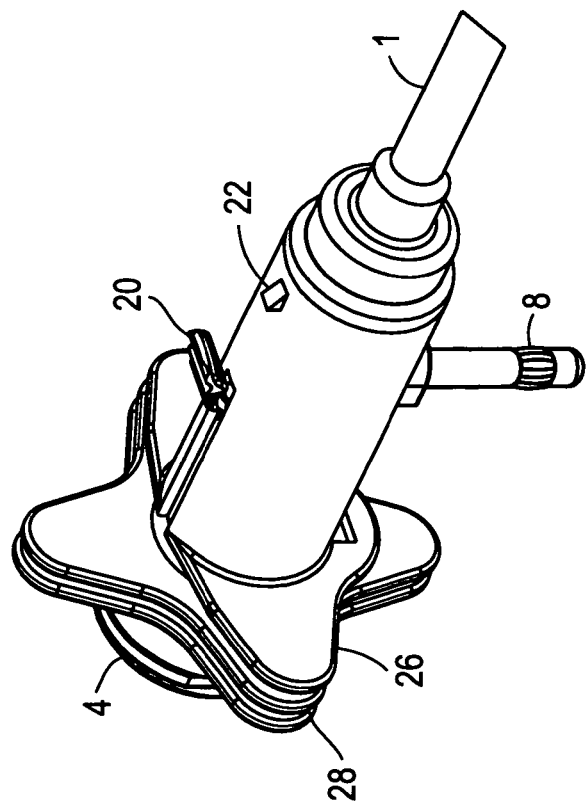
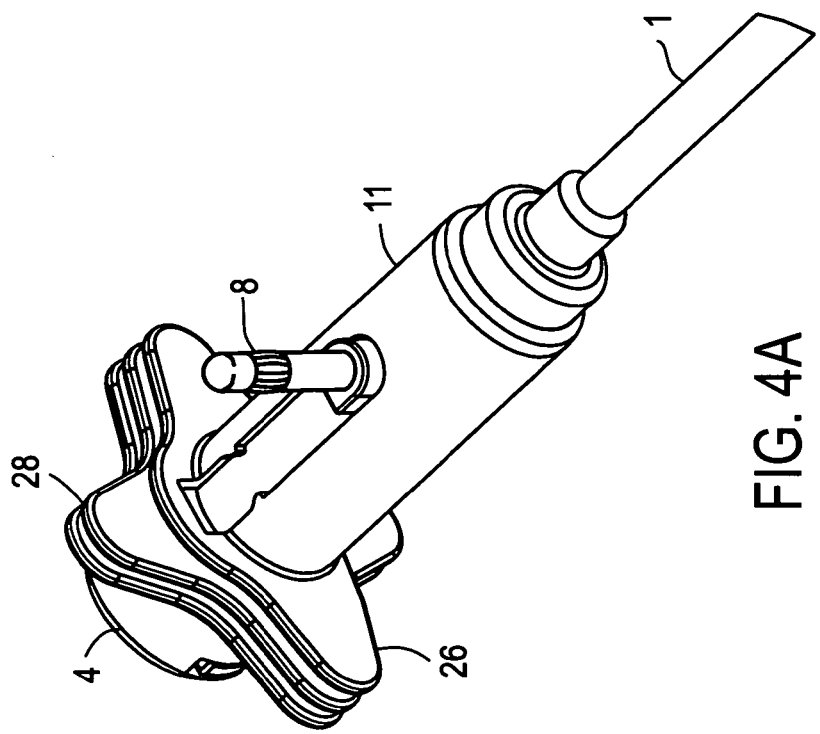
FIG. 4B
FIG. 4A

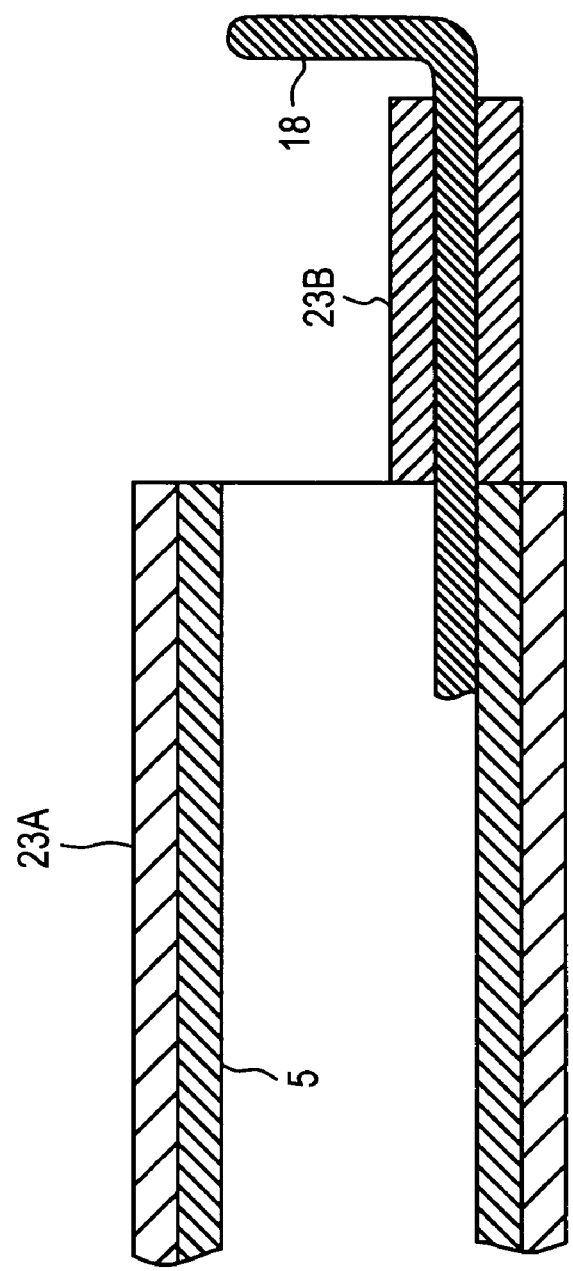

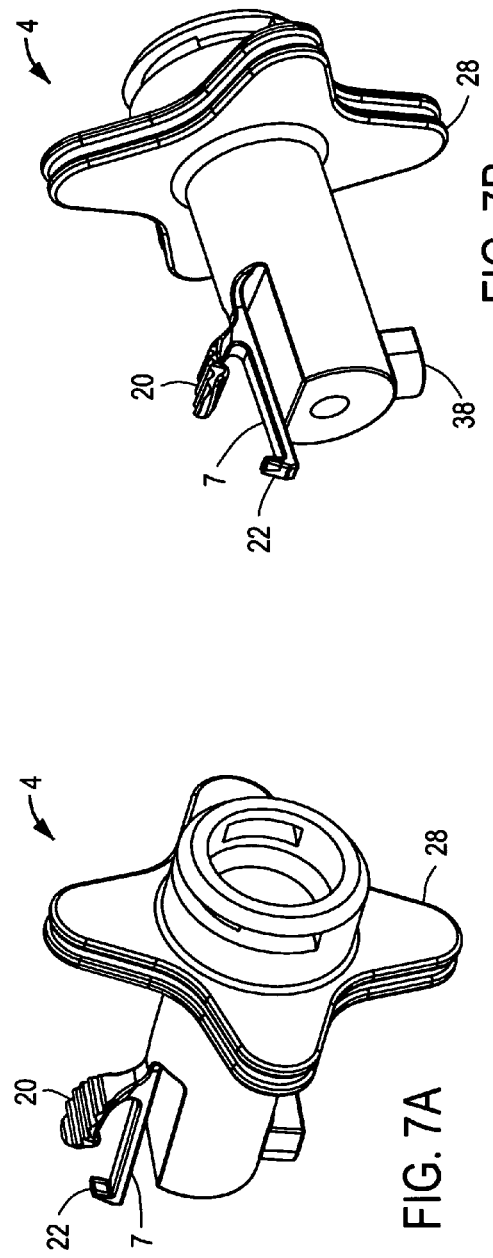
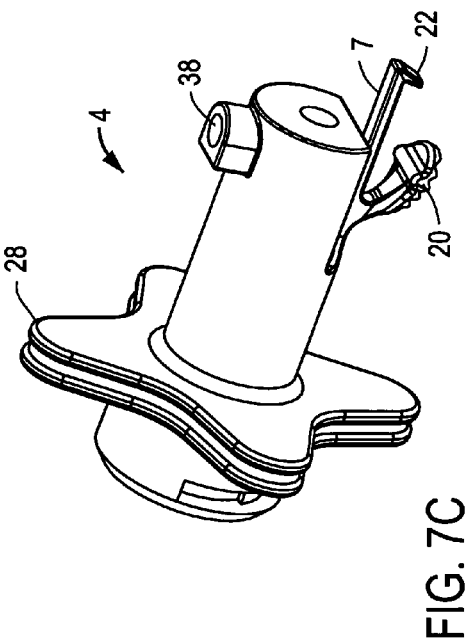
FIG. 7B
FIG. 7C
FIG. 7A

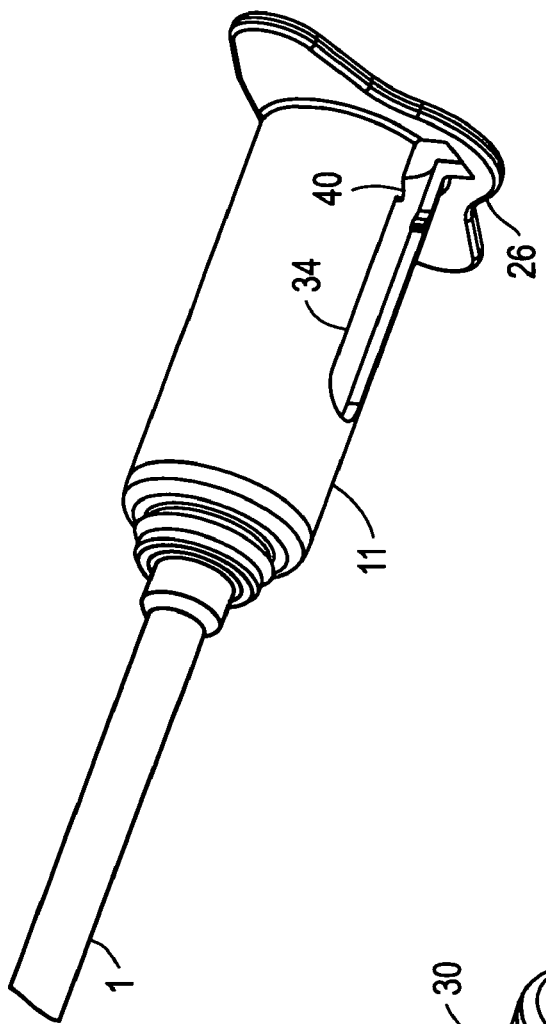
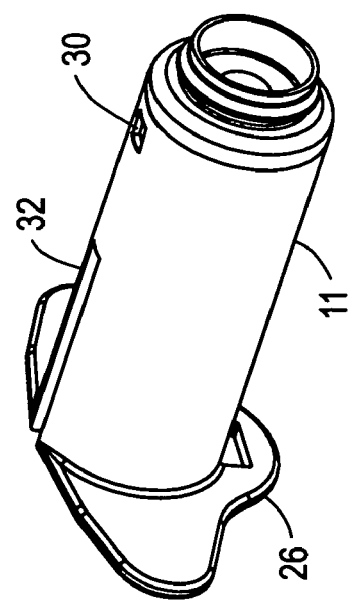
FIG. 9B
FIG. 9A

SECTION F-F

SECTION A-A

SURGICAL INSTRUMENT WITH RETRACTABLE SHEATH

This application claims the benefit of U.S. Provisional Patent application No. 60/508,167, filed on Oct. 1, 2003 and entitled, "Endoscopic Electrosurgical Suction/Irrigation Instrument with Spring Actuated Extendable Sheath," which is incorporated herein by reference.

FIELD OF THE INVENTION

At least one embodiment of the present invention pertains to surgical instruments, and more particularly, to an electrosurgical suction/irrigation instrument with a retractable sheath.

BACKGROUND

Electrosurgery, suction, and irrigation are three important functions commonly used during modern surgical procedures. In the past, each of these functions was accomplished with a separate, dedicated surgical instrument. However, it became apparent that there were advantages to combining some or all of these functions into a single instrument. Such multifunction instruments were developed, therefore, and variations of them are now commonplace in modern surgery.

An instrument which combines electrosurgical, suction, and irrigation features may be referred to as an electrosurgical suction/irrigation instrument. An example of such an instrument includes a handpiece to allow the instrument to be held by a surgeon, and an operational tip connected to the handpiece. The operational tip is used for delivery of electrical current for electrosurgery as well as for channeling fluid for suction and irrigation. A conductive electrode is attached to the distal end of the operational tip, for electrosurgery. In some implementations, a retractable, non-conductive sheath covers the electrode. The sheath serves to protect and expose the distal electrode. The sheath is retracted to expose the electrode when the instrument is needed for electrosurgery and extended to cover the electrode when the instrument is being used for suction or irrigation.

Some designs of electrosurgical instruments make it inconvenient or awkward for the surgeon to extend the sheath or to retract the sheath, or both. For example, certain known designs require the use of two hands to extend or retract the sheath, i.e. one hand to hold the instrument and the other to extend or retract sheath. This limitation is undesirable, since a surgeon is often holding the electrosurgical instrument in one hand and another instrument in the other hand during surgery. It is inconvenient for the surgeon to have to put the other instrument down or to have to request the assistance of another person in order to extend or retract the sheath.

Some electrosurgical devices may move the electrode, while the sheath remains stationary. However, such tools require a specialized corresponding device that interfaces with the actuating electrode assembly. The dependency on an additional component to make an electrosurgical probe function is undesirable, as the additional components tend to be complicated and expensive.

Various other shortcomings are known to be associated with current electrosurgical instruments.

SUMMARY OF THE INVENTION

The present invention includes a surgical instrument that includes a shaft hub, an electrically conductive member, and a sheath. The electrically conductive member has a proximal end mounted to the shaft hub and a distal end including a conductive operating tip. The sheath covers the conductive member so that the operating tip is covered when the sheath is in an extended position and exposed when the sheath is in a retracted position. The sheath hub is coupled to the sheath and is movably engaged with the shaft hub. The surgical instrument further includes a locking mechanism to lock the sheath in the retracted position, and a bias element to bias the sheath toward the extended position.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which:

FIGS. 2A through 2C show different perspective views of the sheath hub and shaft hub when the sheath is extended;

FIGS. 3A and 3B illustrate different views of the electrosurgical suction/irrigation instrument when its sheath retracted;

FIGS. 4A and 4B show different perspective views of the sheath hub and shaft hub when the sheath is retracted;

FIG. 5C shows a partial cross-sectional view of the operating tip of the shaft assembly;

FIGS. 7A through 7C show different perspective views of the shaft hub;

FIGS. 9A and 9B illustrate different perspective views of the sheath hub;

DETAILED DESCRIPTION

Figure 1A:
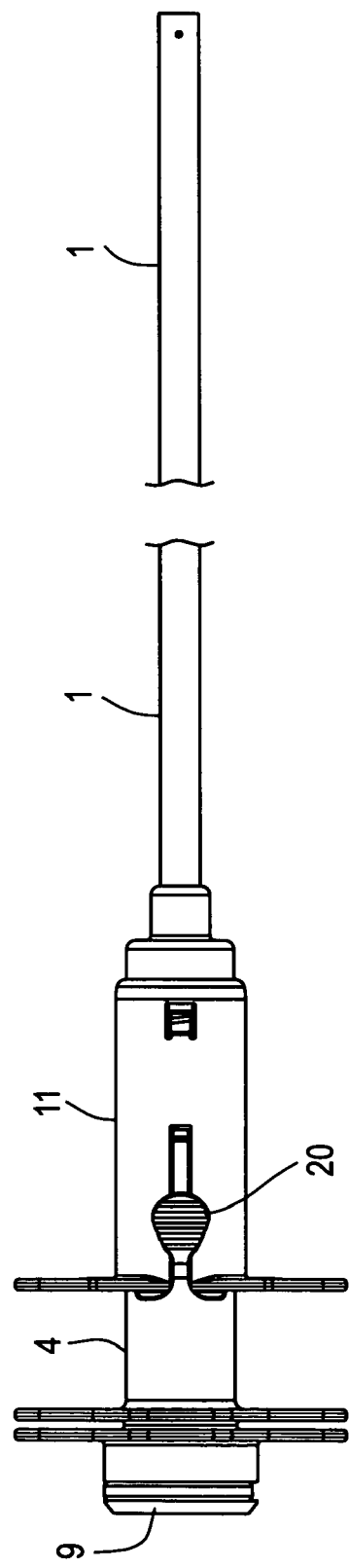
FIGS. 1A and 1B show different views of an electrosurgical suction/irrigation instrument with its sheath extended.

An electrosurgical suction/irrigation instrument (or "probe") with a retractable sheath is described. Note that in this description, references to "one embodiment" or "an embodiment" mean that the feature being referred to is included in at least one embodiment of the present invention. Further, separate references to "one embodiment" or "an embodiment" in this description do not necessarily refer to the same embodiment; however, such embodiments are also not mutually exclusive unless so stated, and except as will be readily apparent to those skilled in the art from the description. For example, a feature, structure, act, etc. described in one embodiment may also be included in other embodiments. Thus, the present invention can include a variety of combinations and/or integrations of the embodiments described herein.

The electrosurgical suction/irrigation instrument introduced herein is useful in performing endoscopic surgical procedures, such as laparoscopy. The instrument allows for suction and irrigation capability through its lumen and has an extendable sheath to allow for more accurate suction and irrigation. The sheath is manually retracted to expose the distal end electrode (which may come in any of various different styles) for electrosurgery. The instrument has an electrical contact which allows for electrosurgery when connected to an electrosurgical generator.

In certain embodiments, as described further below, the instrument has a sheath hub, to which the sheath is attached, which is fully retracted and immovable when a latch is engaged with an interlocking mechanism on the sheath hub. The sheath hub is extended by pushing a proximally located button which releases the latch from the interlocking mechanism, and a spring or other bias element pushes the sheath hub to its biased extended position. Noting that with one hand it is easier to retract the sheath hub than it is to extend it, the bias element allows for true one-handed operation. The user no longer needs two hands to operate an instrument with an extendable sheath, as experienced with current similar instruments. Additionally, the instrument has a rotator knob which allows for instrument rotation in relation to the handpiece assembly to which it is attached.

Having a movable sheath is advantageous in that the probe can be used with an inexpensive endoscopic instrument that does not require special features to expose and cover the distal electrode. A probe with a movable sheath can be simply attached to a corresponding endoscopic instrument, and the electrode exposure and coverage is governed by sheath movement, not mechanisms within the endoscopic instrument, thus making the probe independent from the endoscopic instrument.

The spring actuation allows for true one-handed extension and retraction of the electrosurgical instrument sheath. In general, it is easy to retract the sheath hub with one's fingers, but it is more difficult and less ergonomic to extend the sheath with one hand using a pushing motion. To eliminate the need for such cumbersome manipulation, a spring or other bias element is implemented to return the sheath to its default biased forward position. Known existing electrosurgical instruments do not include a retractable and extendable sheath that incorporates biased (e.g., spring) actuation. In certain instruments, the sheath must be extended manually, which often requires another hand to accomplish. In addition, the instrument described below uses a single lumen for both suction/irrigation and electrosurgery, in contrast with other electrosurgical instruments.

In the embodiments described below, the electrode remains stationary, while the sheath is extendable and retractable. Other electrosurgical devices may incorporate spring actuation to move the electrode, where the sheath remains stationary. However, such tools require a specialized corresponding device that interfaces with the actuating electrode assembly. The dependency on another component to make an electrosurgical probe function properly is undesirable.

Figure 1B:
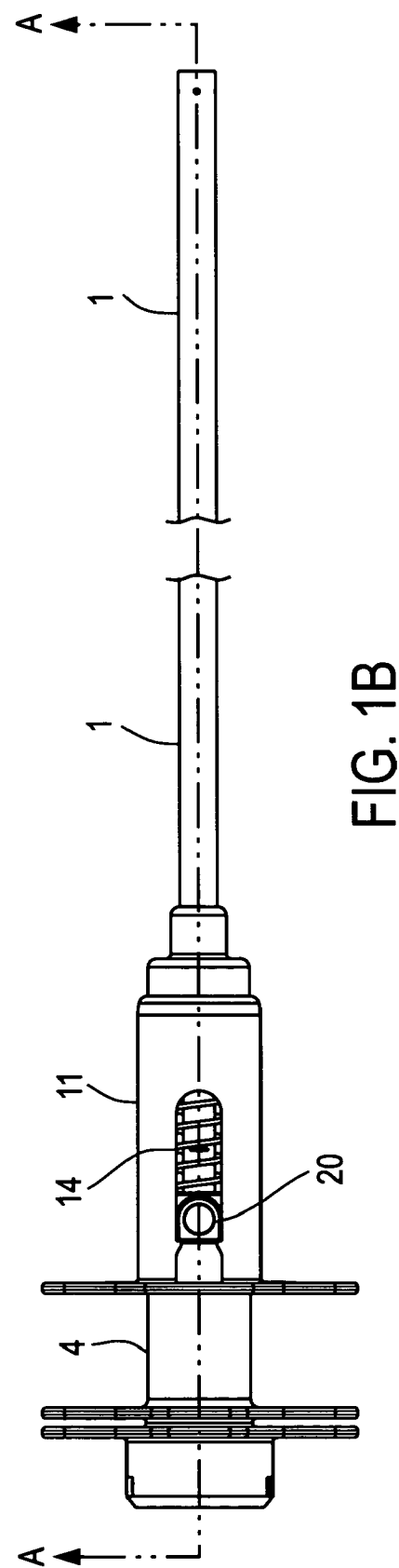

FIGS. 1A through 17 show the electrosurgical suction/irrigation instrument introduced herein according to an embodiment of the invention. FIGS. 1A and 1B show two views of the electrosurgical suction/irrigation instrument with its sheath 1 extended. FIGS. 3A and 3B illustrate two corresponding views of the electrosurgical suction/irrigation instrument with its sheath 1 retracted.

The instrument includes two major assemblies: a shaft assembly (FIGS. 5A and 5B) and a sheath assembly (FIG. 6), which is slidably coupled to the shaft assembly. The shaft assembly includes: a shaft hub 4, an electrically conductive tube 5 (partially covered by an insulative jacket), an electrically conductive post 8, a retainer clip 9, and an electrode 18 (also partially covered by an insulative jacket). The sheath assembly includes a sheath hub 11, a retractable tubular sheath 1, an o-ring 13, and an o-ring cover 15. The instrument also includes a spring 14 or other bias element, to bias the sheath toward the extended position, as described further below.

FIGS. 2 and 4 illustrate the integration of, and cooperation between, the shaft hub 4 and the sheath hub 11. In particular, FIGS. 2A through 2C show the sheath hub 11 and shaft hub 4 when the sheath 1 is extended. FIGS. 4A and 4B show the sheath hub 11 and shaft hub 4 when the sheath 1 is fully retracted.

Figure 2D:
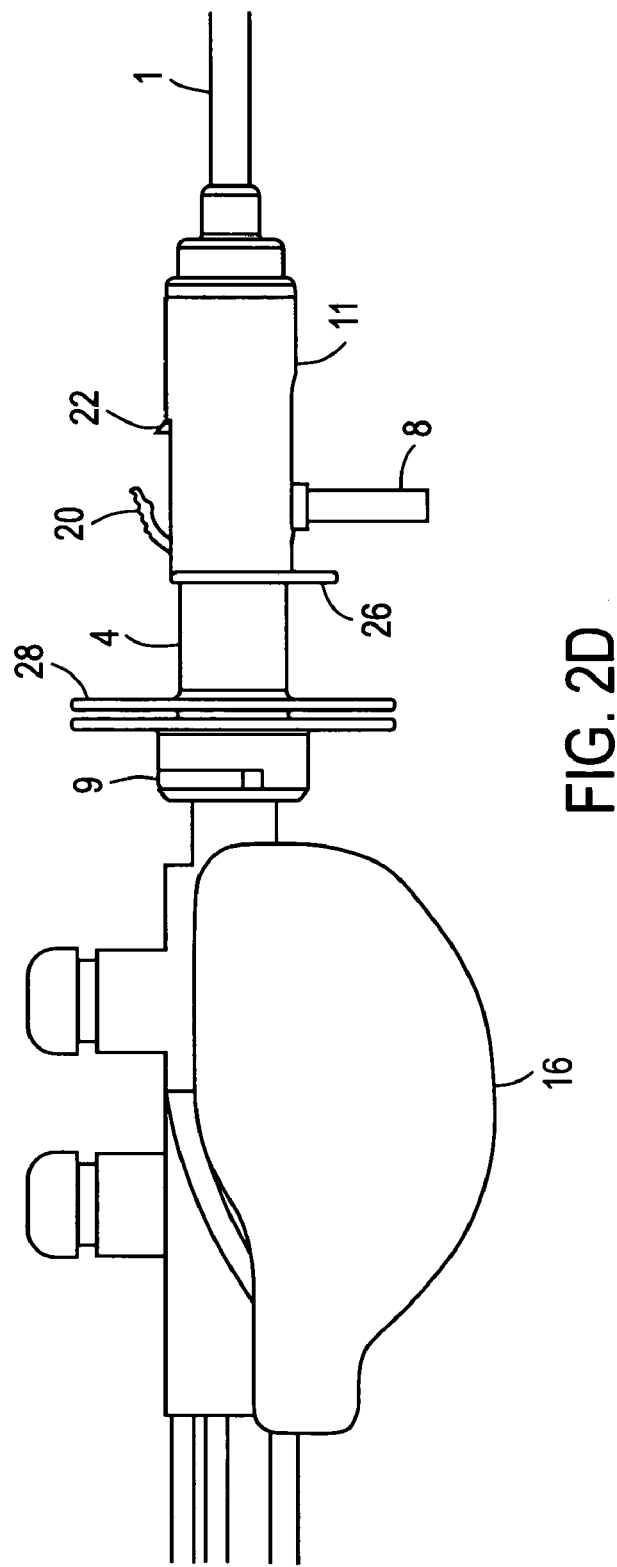
FIG. 2D illustrates the connection of the shaft hub to the handpiece.
Figure 5A:
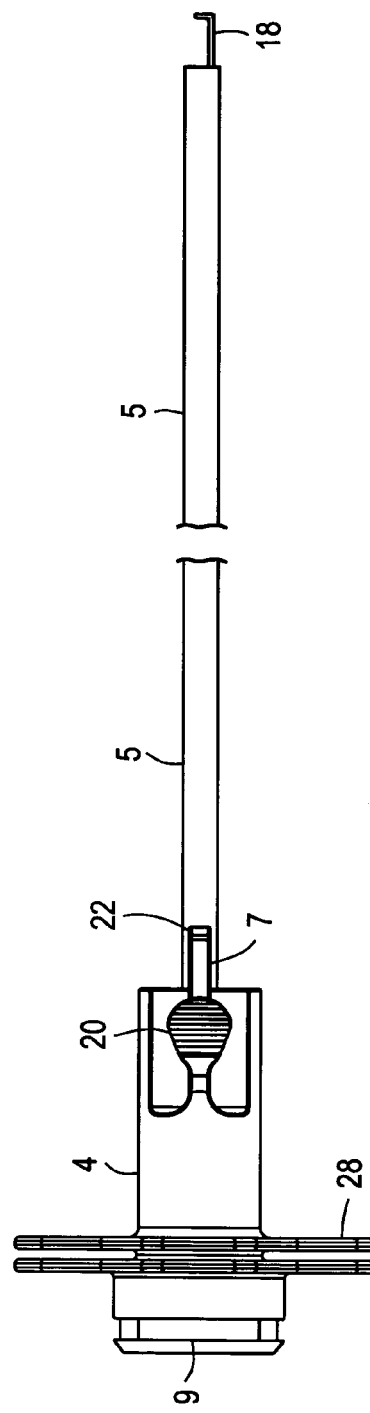
FIGS. 5A and 5B show different views of the shaft assembly.
Figure 5B:
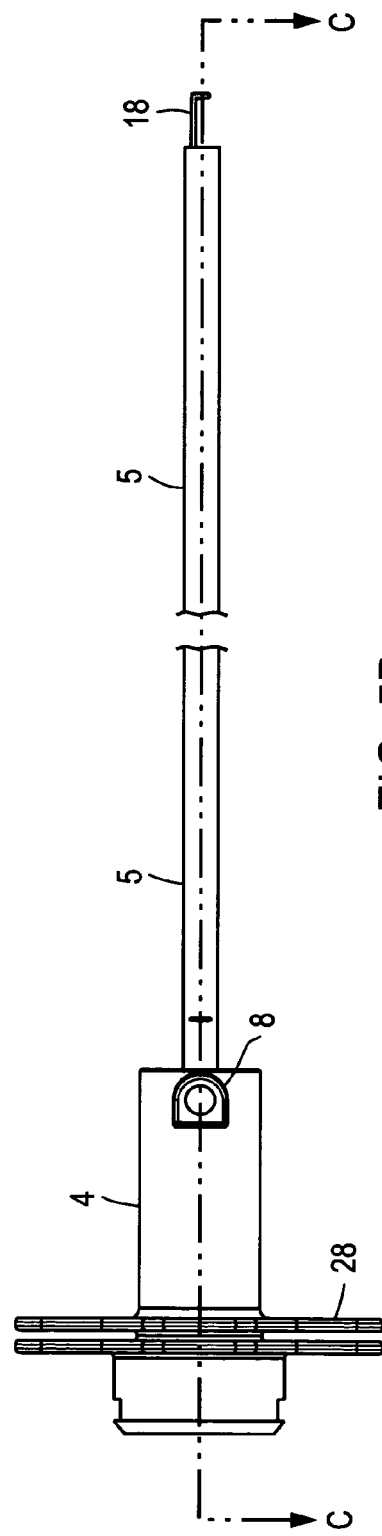
Figure 11:
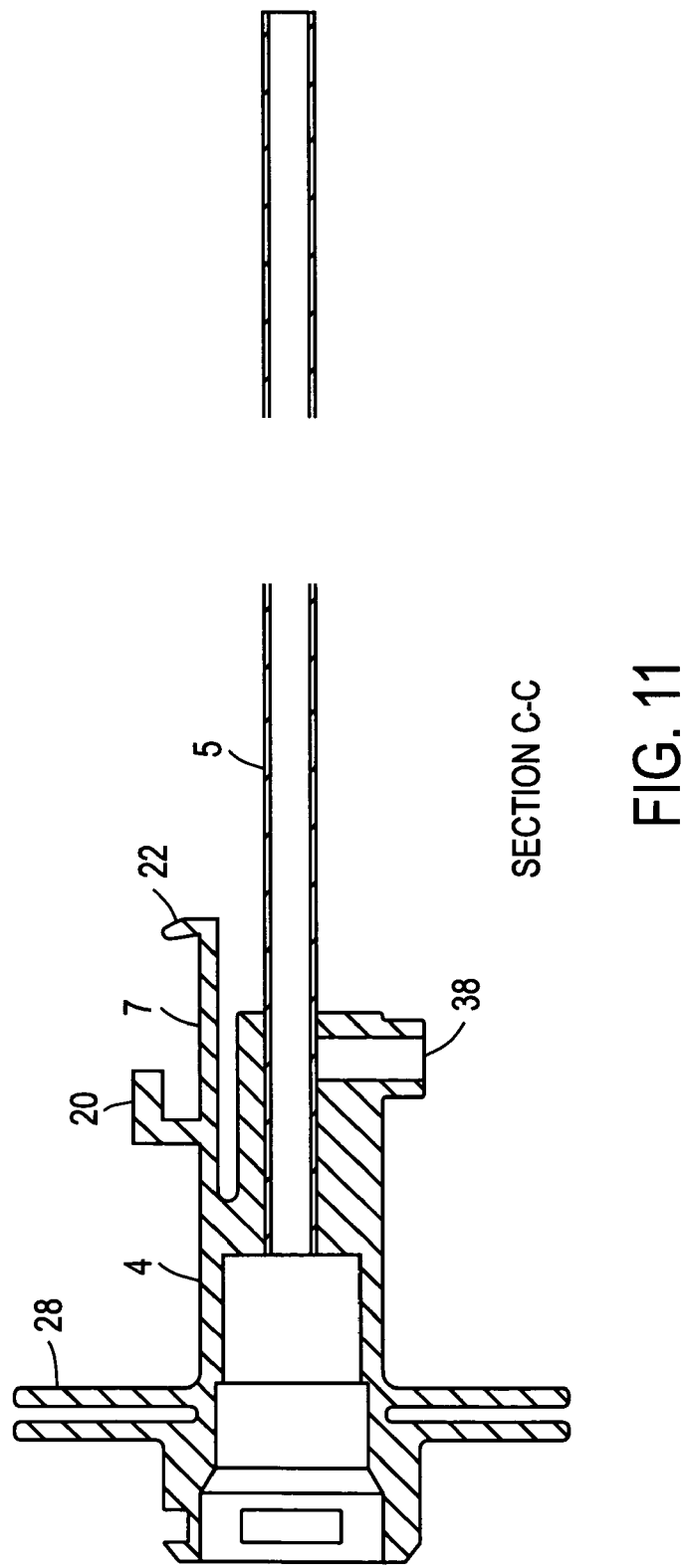
FIG. 11 shows a cross-sectional view of the shaft assembly.

Referring now to the components of the shaft assembly, different views of the shaft assembly are shown in FIGS. 5 and 11. The shaft hub 4 may be formed from molded plastic. The shaft hub 4 is removably connectable at its proximal end to a handpiece 16 (FIG. 2D), from which suction and irrigation are controlled. The shaft hub 4 serves as an attachment to a suction/irrigation system. The distal end of the shaft hub 4 connects to the proximal end of the conductive tube 5. The conductive tube 5 is covered with a thin insulative jacket 23A (shown in FIG. 5C; not shown in FIGS. 5A, 5B and 11), except for the portion of its proximal end which is internal to the shaft hub 4 when these two pieces are mated together. A conductive electrode 18 is attached to, or formed integral with, the distal end of the conductive tube 5. All but the distal end of the electrode 18 is covered with a thin insulative jacket 23B (shown in FIG. 5C; not shown in FIGS. 5A, 5B and 11). The proximal opening of the shaft hub 4 (FIGS. 2A through 2C) connects with the distal end of the handpiece 16 of the suction/ irrigation system (FIG. 2D). An example of a connection between the shaft hub 4 and the handpiece 16 is via a snap fit with retainer clip 9, which may be a flexible C-clip, providing the snap feature onto the handpiece 16. An alternative method of connection is where the shaft hub 4 is threaded onto the handpiece, which also has threads, in which case retainer clip 9 is not necessary.

FIGS. 7 and 8 illustrate different views of the shaft hub 4. The shaft hub 4 includes, near its proximal end, a rotator knob 28 extending radially outward from an outer surface of the shaft hub 4, to allow rotation of the instrument in relation to the handpiece. The shaft hub 4 also includes, near its distal end, a built-in flexible beam 7 that extends parallel to the conductive tube 5. The flexible beam 7 has a push button 20 formed thereon and further has a latch 22 formed thereon at its distal end. The latch 22 and push button 20 are used to lock and unlock, respectively, the sheath assembly from its retracted position.

Referring to FIGS. 5A and 5B, the electrically conductive tube 5 has a proximal end mounted to the distal end of the shaft hub 4 (by an overmolding process, for example) and a distal end with a conductive operating tip (electrode 18) formed thereon. The electrically conductive tube 5 is used to conduct electricity to the electrode 18 as well as to channel irrigation solution from an irrigation reservoir to the operative site and to channel fluid from the operative site to a waste container. An insulative cover 23A (FIG. 5C) is disposed around a portion of an exterior surface of the conductive tube 5, excluding the operating tip.

The electrically conductive post 8 (FIGS. 2 and 4) is mounted to the shaft hub 4, in electrical contact with the conductive tube 5. The conductive post 8 is configured to be coupled to a flexible electrical conductor (e.g., a cable) to receive power from an electrosurgical generator. The conductive tube 5 is mounted to the shaft hub 4 far enough proximally so that the conductive post 8, when screwed and glued into its receptacle, makes contact with the conductive tube 5. This allows the current to travel from the post 8, down the tube 5, to the distal electrode 18.

Figure 6:
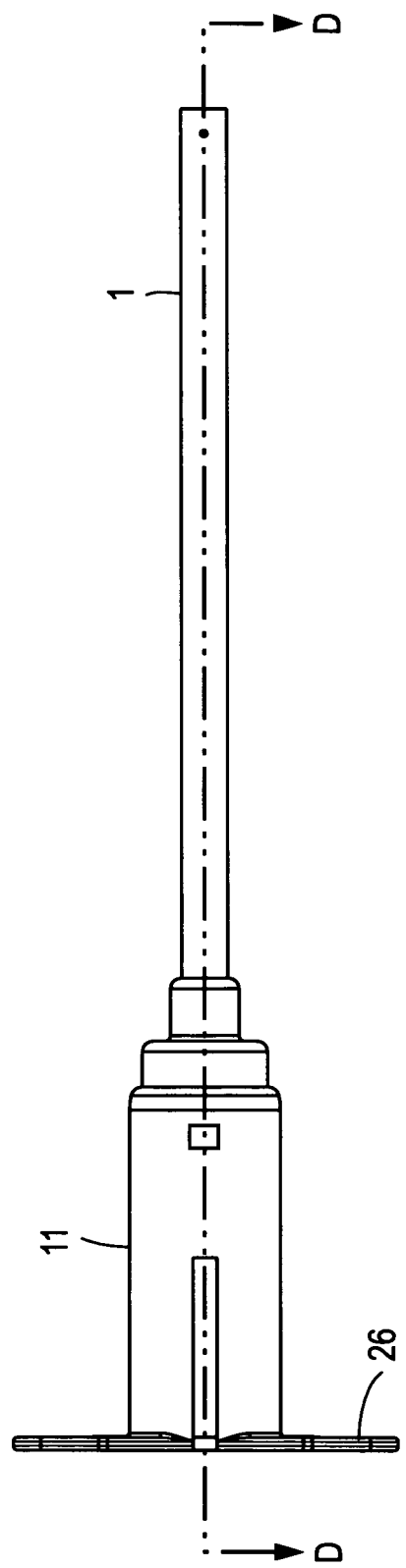
FIG. 6 illustrates the sheath assembly.
Figure 8D:
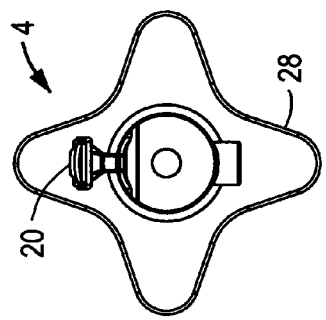
FIGS. 8A, 8B, 8D, and 8E illustrate various orthogonal views of the shaft hub.
Figure 8A:
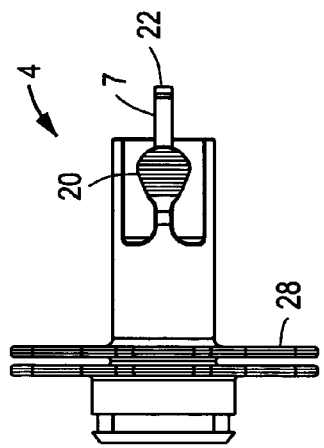
Figure 8C:
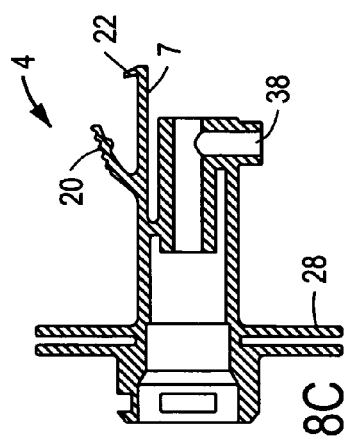
FIG. 8C shows a cross-sectional view of the shaft hub.
Figure 8E:
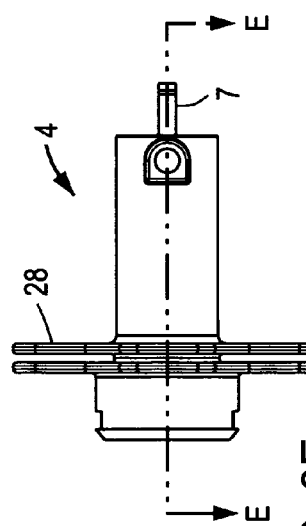
Figure 8B:
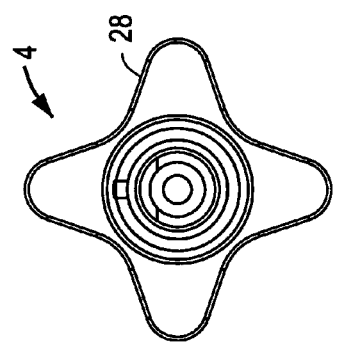
Figure 12:
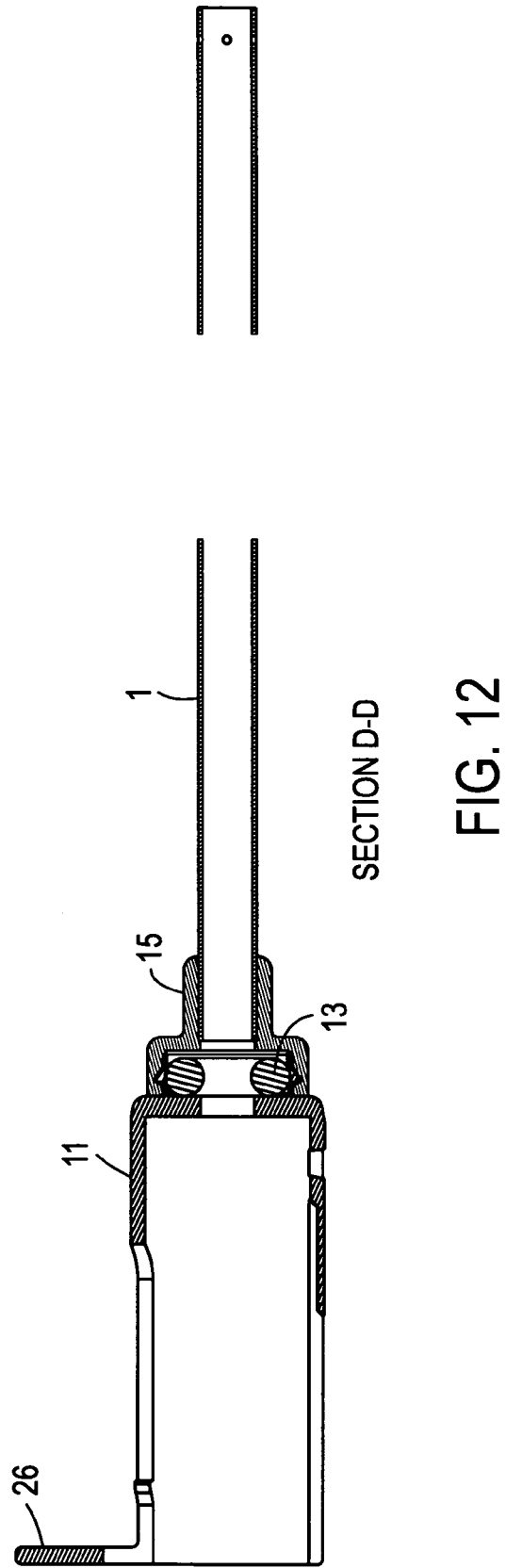
FIG. 12 shows a cross-sectional view of the sheath assembly.

Referring now to the sheath assembly, different views of the sheath assembly are shown in FIGS. 6 and 12. The sheath assembly includes a tubular non-conductive sheath 1, a sheath hub 11, and an o-ring 13. The sheath 1 covers the conductive tube 5 and covers the operating tip (electrode 18) when the sheath 1 is in an extended position, whereas the operating tip is exposed when the sheath 1 is in the retracted position. The sheath 1 may have vent holes located distally for irrigation dispersion and side venting during suction.

Figures 10A, 10B, 10C, 10D, 10E:
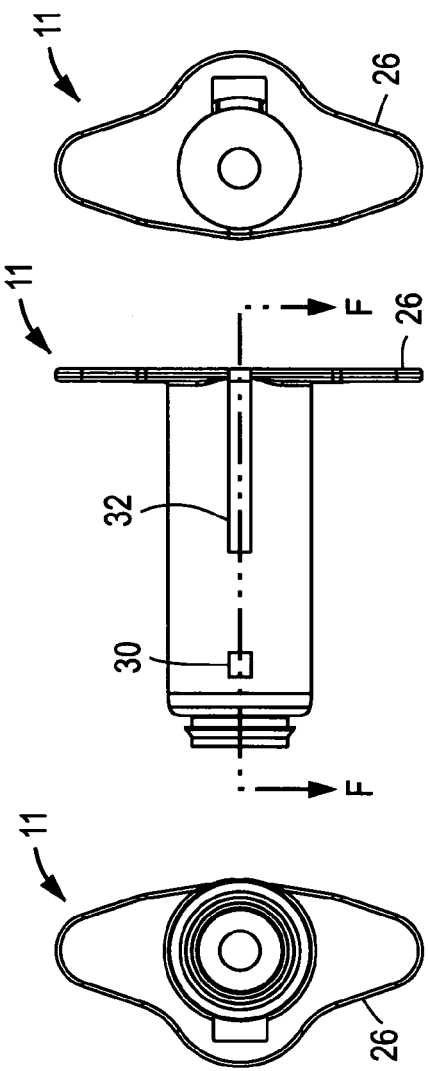
FIGS. 10A through 10E illustrate various orthogonal views of the sheath hub.
Figure 10F:
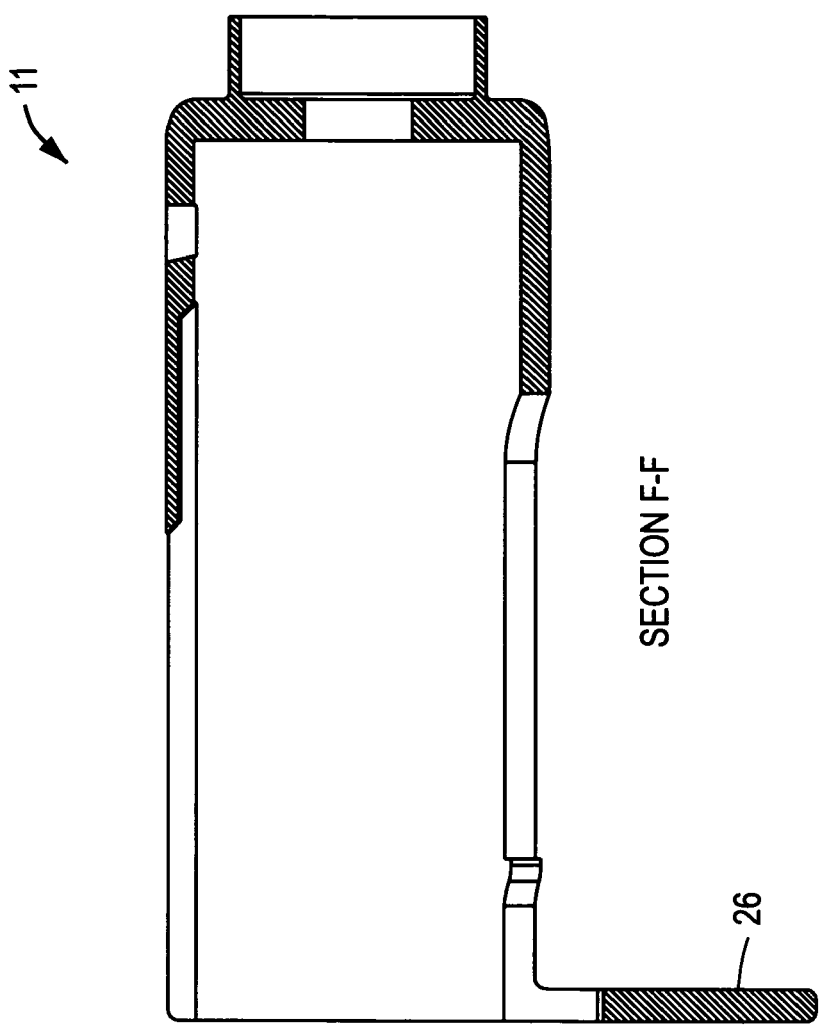
FIG. 10F shows a cross-sectional view of the sheath hub.

The sheath hub 11, shown in detail in FIGS. 9 and 10, may be formed from molded plastic. The sheath 1 is coupled to the o-ring cover 15 by, for example, glue or overmolding process. The o-ring cover 15 is coupled to the sheath hub 11 by, for example, glue or a solvent bond. The sheath hub 11 has an internal o-ring 13 (FIG. 12) to prevent pneumatic loss between the sheath 1 and the conductive tube 5 during a surgical procedure.

Figure 13A:
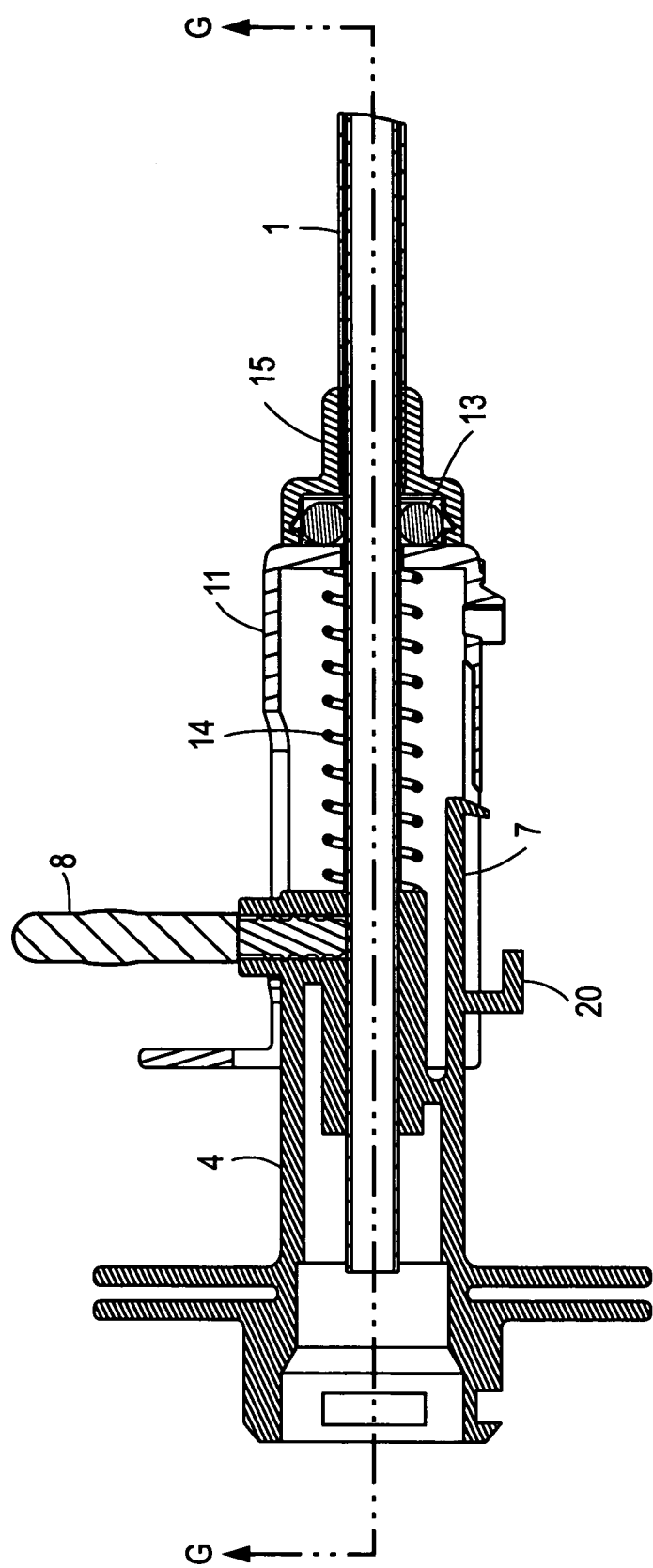
FIG. 13A shows a partial cross-sectional view of the electrosurgical suction/irrigation instrument with its sheath extended.
Figure 13B:
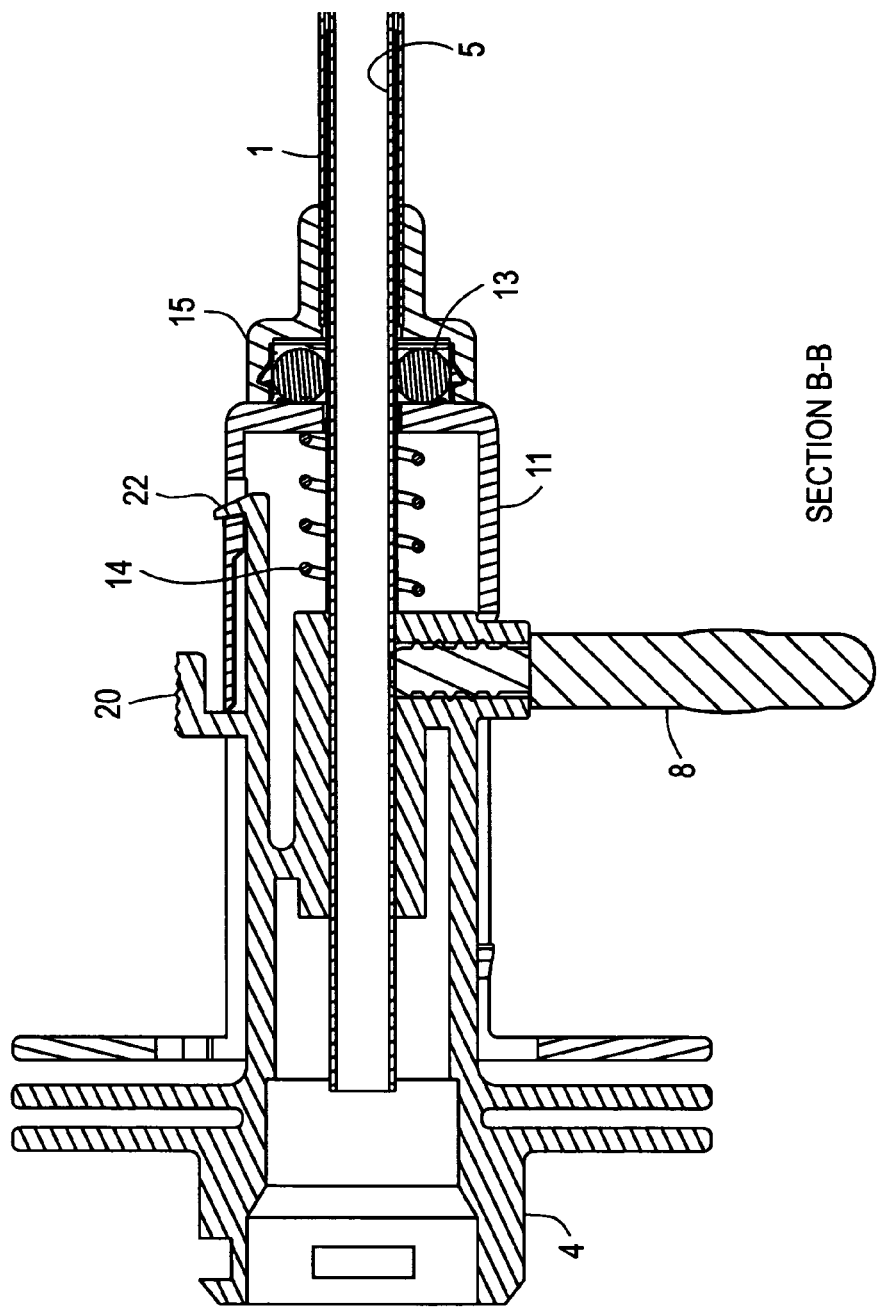
FIG. 13B shows a partial cross-sectional view of the electrosurgical suction/irrigation instrument with its sheath retracted.
Figure 14:
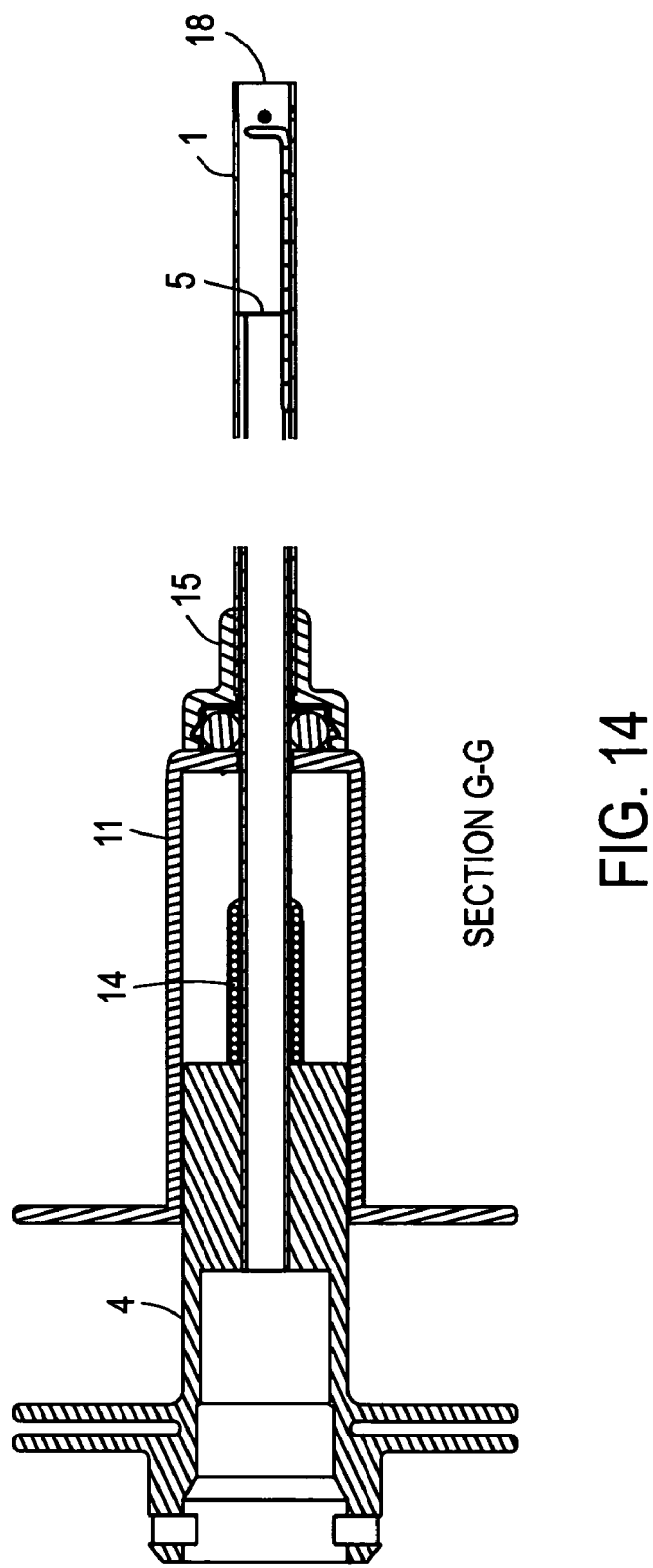
FIG. 14 shows a cross-sectional view of the sheath and shaft assemblies, with the sheath extended.
Figure 15:
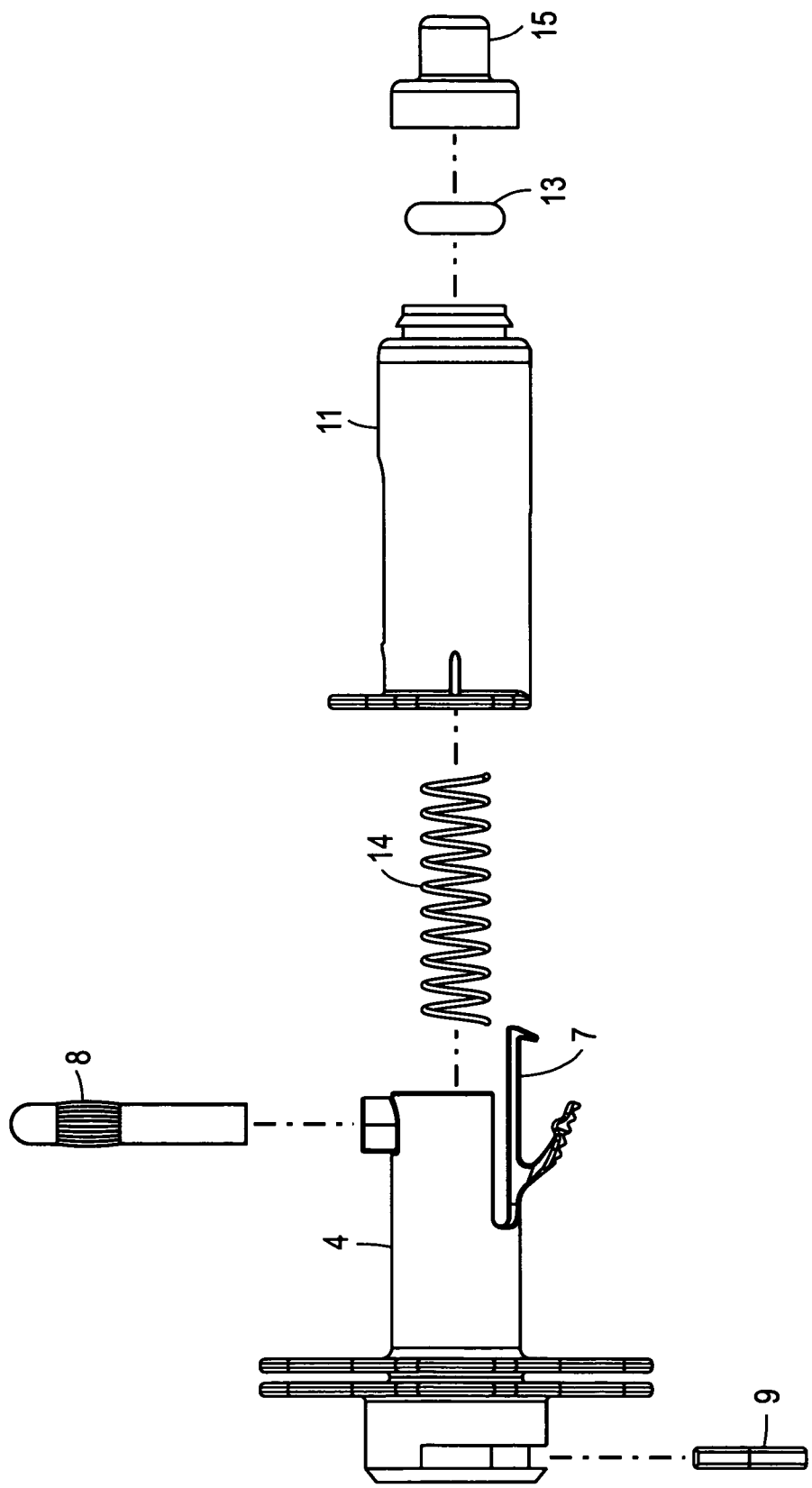
FIG. 15 is an exploded view of the shaft hub and the sheath hub with other components.
Figure 16:
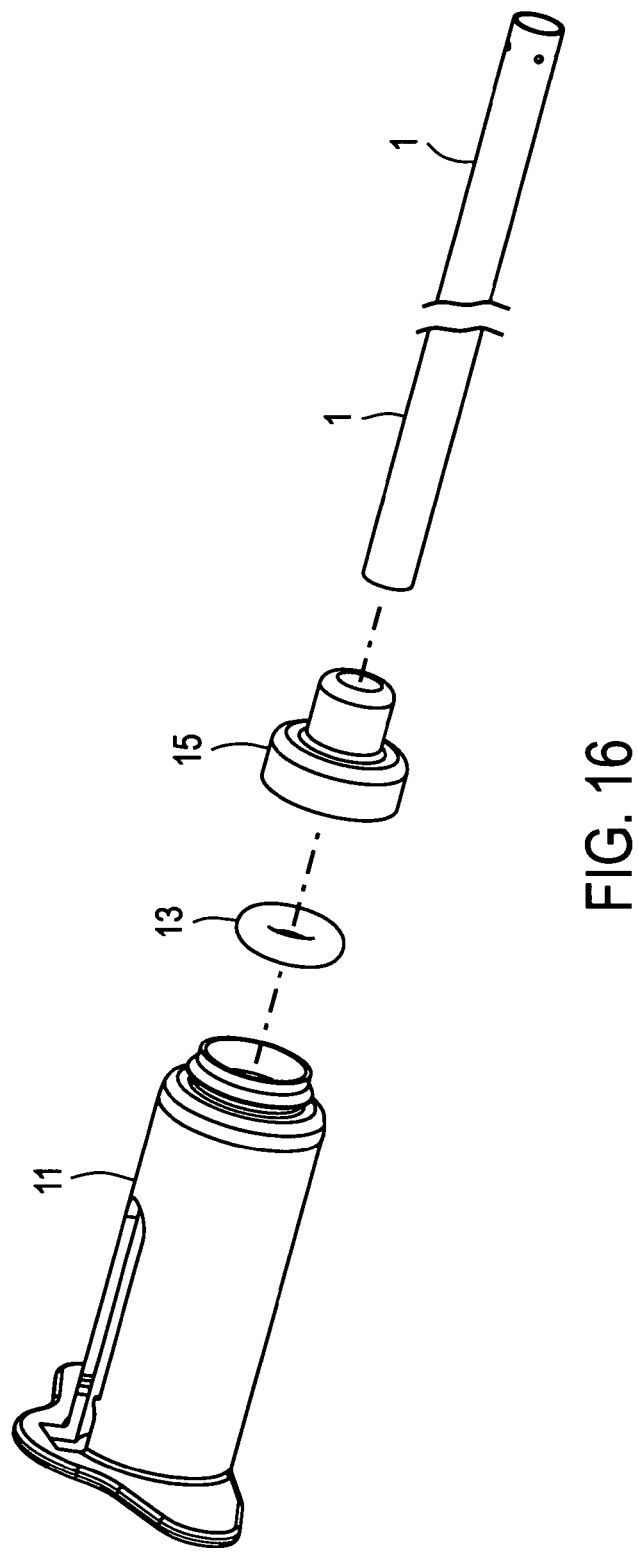
FIG. 16 is an exploded view of the sheath assembly.
Figure 17:
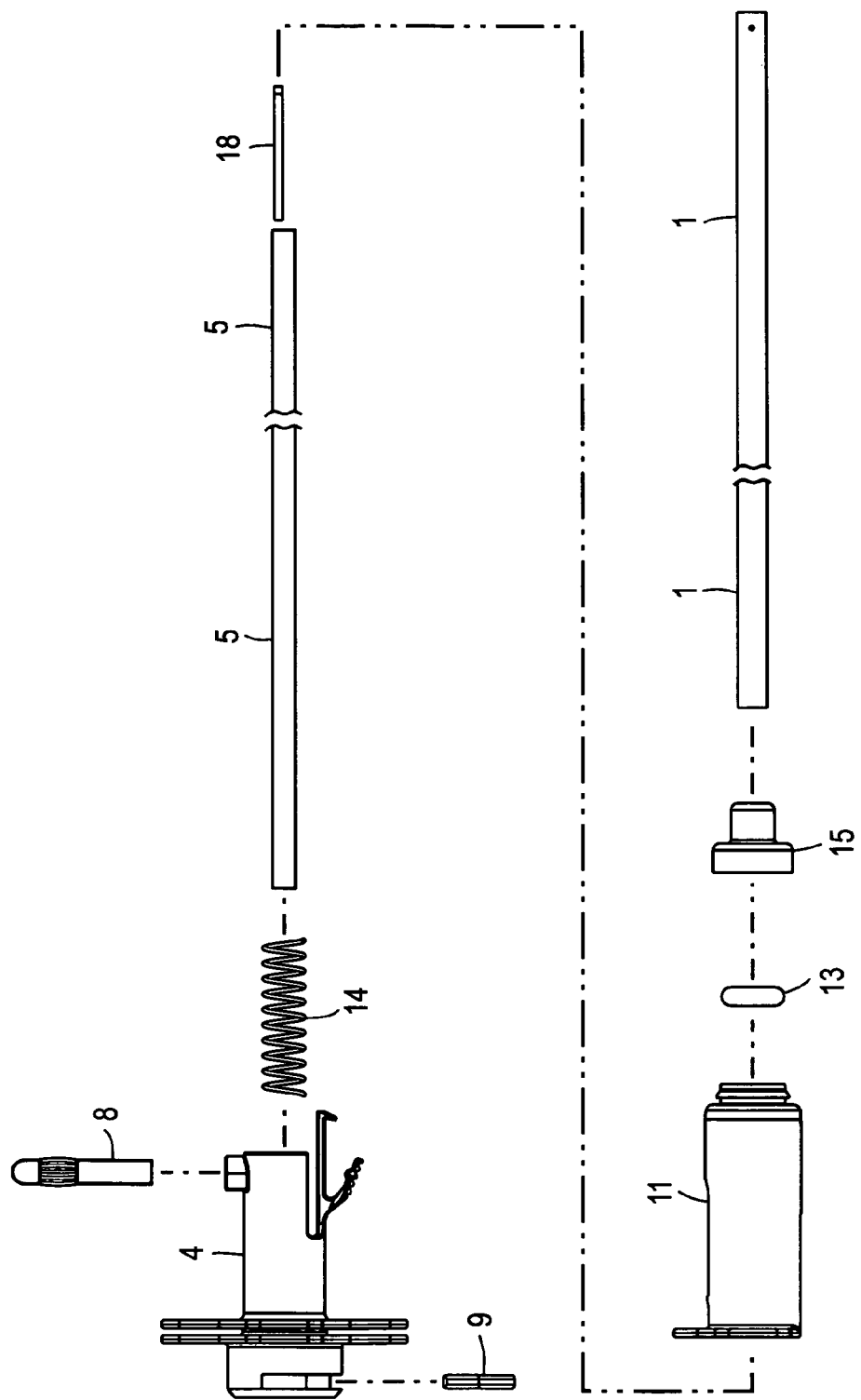
FIG. 17 is an exploded view the electrosurgical suction/irrigation instrument.

The sheath hub 11 has a retractor flange 26 that extends radially outward from an outer surface of the sheath hub 11. The retractor flange 26 is disposed against a rotator knob 28 when the sheath 1 is in the fully retracted position (FIGS. 4 and 13B). The retractor flange 26 facilitates retraction of the sheath 1 in response to an axial force applied to the retractor flange 26. As shown (see, e.g., FIGS. 2A and 4A) and as further described below, the retractor flange 26 has an outer edge that is at least partially conformal with an outer edge of the rotator knob 28 on the shaft hub 4, such that the retractor flange 26 and the rotator knob 28 form a substantially monolithic shape when the retractor flange 26 is disposed against the rotator knob 28 (when the sheath 1 is fully retracted). This will provide more surface area for knob rotation.

The top of the sheath hub 11 further includes a latch opening 30 (FIG. 10C) which engages the latch 22 when the sheath 1 is retracted to its fully retracted position, to lock the sheath 1 in the fully retracted position. The top of the sheath hub 11 also has a slot 32, axially in line with the latch opening 30, through which the button 20 slideably extends relative to the sheath hub 11. The slot 32 provides the button 20 on the flexible beam 7 with a path in which to slide when the sheath assembly is retracted. Depressing the button 20 causes flexing of the flexible beam 7 to disengage the latch 22 from the latch opening 30, to unlock the sheath 1 from the fully retracted position.

The spring 14 (FIGS. 13 through 15) allows the sheath hub 11 to extend forward with a push of the button 20, from the fully retracted position. The spring 14 is disposed around the conductive tube 5 between the shaft hub 4 and an inner surface of the sheath hub 11, to bias the sheath 1 toward the extended position. The spring 14 is located in the hollow interior of the sheath hub 11 and is axially aligned with the conductive tube 5. The spring 14 acts upon the distal surface of the shaft hub 4 and the distal internal surface of the sheath hub 11. The spring 14 compresses and resists the retraction of the sheath hub 11. Once the sheath hub 11 is fully retracted, the latch 22 on the shaft hub 4 engages with the latch opening 30 in the sheath hub 11 (FIGS. 4B and 13B). Once engaged, the sheath 1 cannot move axially with respect to the rest of the instrument. When the button 20 is pressed and the latch 22 is disengaged (due to the flexible beam 7 flexing downward), the spring 14 pushes the sheath hub 11 to its default biased position (FIGS. 2 and 13A). The spring 14 is designed to be stiff enough so that the distal electrode 18 is not unintentionally exposed during probe insertion into a cannula, but soft enough so that it is easy and ergonomic to retract the sheath hub 11. As noted, a different form of bias element may be used instead of the spring 14 in various embodiments of the invention, such as an elastic material (e.g., rubber), a flexible beam spring molded into the plastic shaft hub 4, pneumatic pressure, etc.

The shaft hub 4 comprises, near its distal end, a receptacle 38 (FIGS. 7C and 11) to receive the conductive post 8. The receptacle 38 for the post 8 is a protrusion near the distal end of the shaft hub 4. The conductive post 8 may include threading to allow the conductive post 8 to be screwed into the receptacle 38 so that the conductive post 8 is held in contact with the electrically conductive tube 5. In certain embodiments, the receptacle is "aggressively" threaded. In other words, the receptacle 38 has no threading prior to the first mating between the conductive post 8 and the receptacle 38; however, the relative softness of the receptacle material (e.g., molded plastic) and the aggressive threading of the conductive post 8 enable threading to be created in the receptacle by the first mating.

The bottom of the sheath hub 11 has a slot 34 (FIG. 9B), which provides the protrusion for the conductive post 8 (i.e., the receptacle 38) with a path in which to slide when the sheath assembly is retracted. There is a detent 40 on the bottom slot 34 that acts as a physical stop and dictates how far forward the sheath assembly can extend once the button 20 is activated and the latch 22 is released. This embodiment is also designed so that the sheath hub 11 cannot be removed.

As noted above, at the proximal end of the sheath hub 11 is a built-in retractor flange 26 (FIG. 9). The retractor flange 26 generally has the same overall shape as the rotator knob 28 on the shaft hub 4; however, the retracted flange 26 does not have a top section as the rotator knob 28 has (FIG. 7), so as not to interfere with activation of the release button 20. When the sheath hub 11 is fully retracted, the retractor flange 26 is stacked up against the rotator knob 28. In that event, the rotator knob 28 and retractor flange 26 together essentially form a thicker rotator knob (FIG. 4), which is easier to grab and rotate.

The method of assembling and integrating the shaft hub assembly and sheath hub assembly is as follows, according to certain embodiments of the invention. On the retractor flange 26 of the sheath hub 11, there are two openings to allow the sheath hub 11 to slide over the beam 7/button 20 and protrusion of the shaft hub 4 (FIG. 9). The spring 14 is mounted coaxially over the insulated conductive tube 5, and the sheath hub 11 is slid over the shaft hub 4. Then the conductive post 8 is screwed and glued into the receptacle 38 in the shaft hub 4 until the threaded end of the post 8 makes pressure contact (and electrical contact) with the conductive tube 5, thus creating an electrical path for the current.

FIGS. 18 through 32 show three alternative embodiments of the invention. Each of these embodiments is generally the same as the embodiment described above, with exceptions as noted below and as apparent from the Figures.

Figure 19:
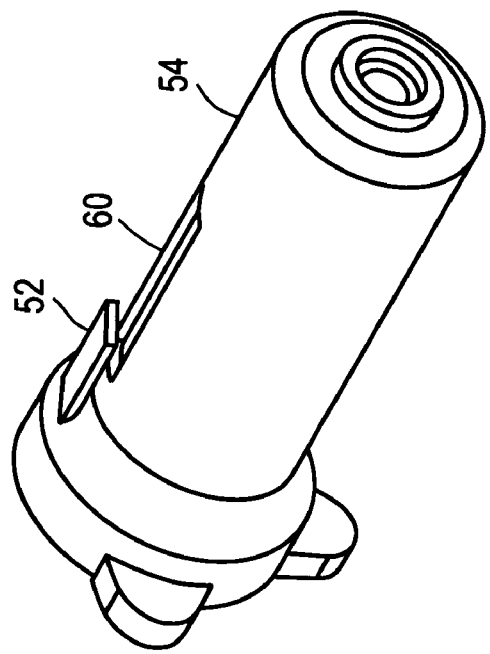
FIG. 19 shows a perspective view of the sheath hub according to the first alternative embodiment of the invention.
Figure 18:
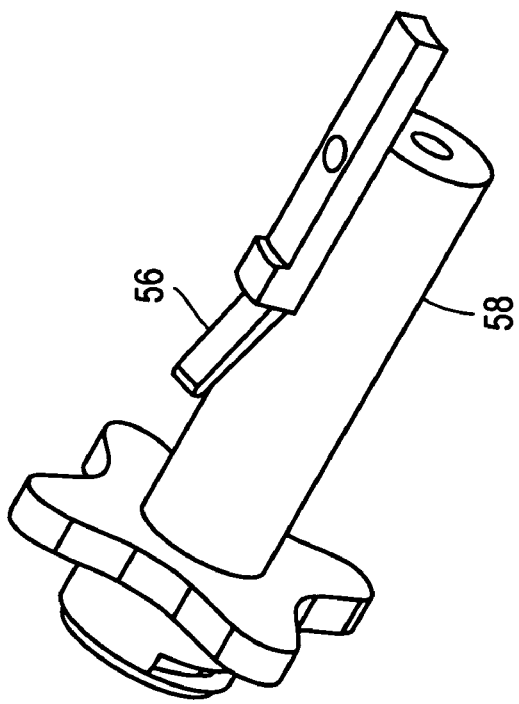
FIG. 18 shows a perspective view of the shaft hub according to a first alternative embodiment of the invention.
Figure 21:
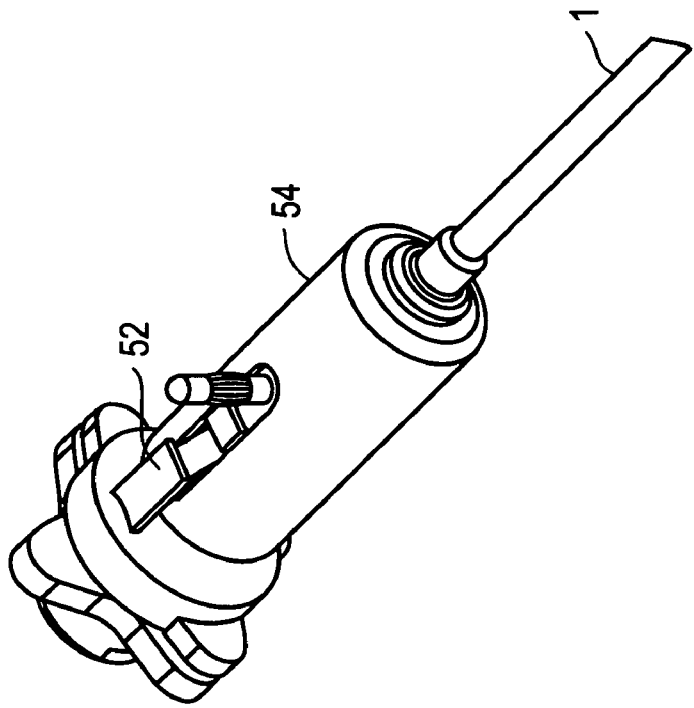
FIG. 21 shows a perspective view of the sheath hub and shaft hub according to the first alternative embodiment of the invention, when the sheath is retracted.
Figure 20:
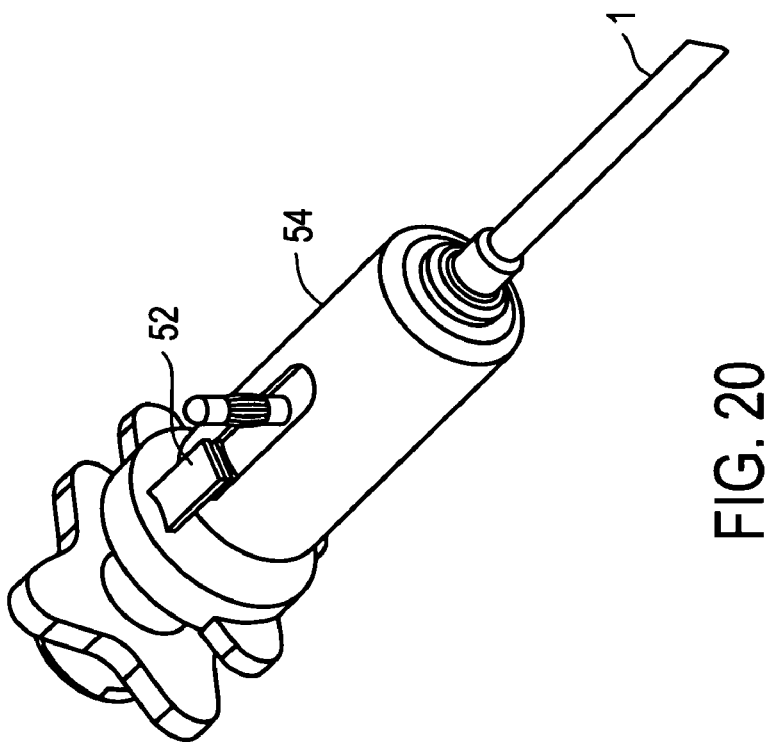
FIG. 20 shows a perspective view of the sheath hub and shaft hub according to the first alternative embodiment of the invention, when the sheath is extended.
Figure 22:
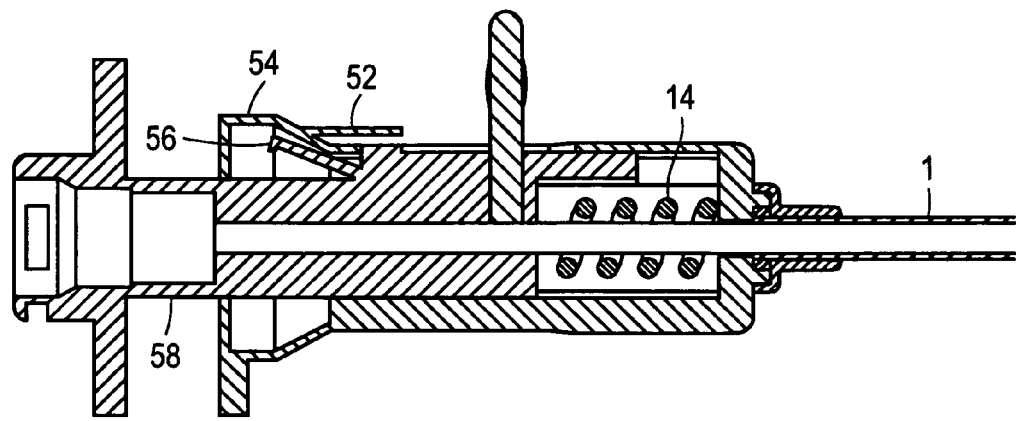
FIG. 22 shows a partial cross-sectional view of the electrosurgical suction/irrigation instrument according to the first alternative embodiment of the invention, when the sheath is extended.
Figure 23:
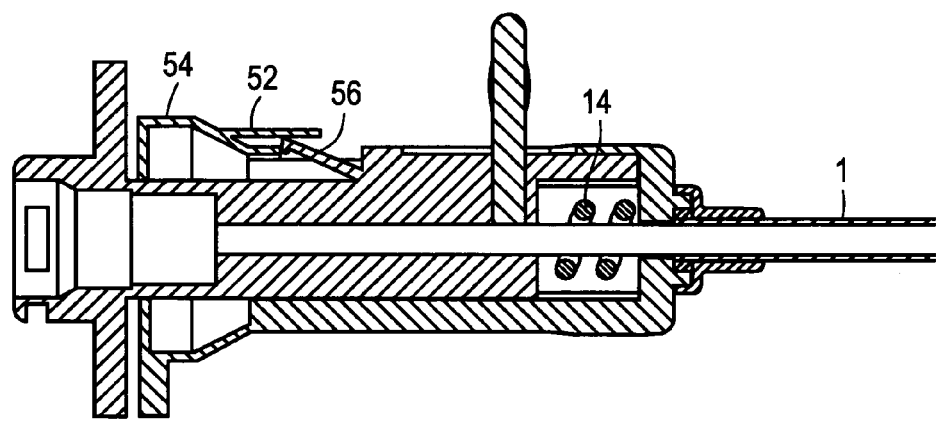
FIG. 23 shows a partial cross-sectional view of the electrosurgical suction/irrigation instrument according to the first alternative embodiment of the invention, when the sheath is retracted.

FIGS. 18 through 23 show a first alternative embodiment of the invention. In this embodiment, a locking mechanism is different from that described above. In particular, the release button 52 is located on the moving part, i.e., the sheath hub 54, which is shown in FIG. 19. The release button 52 on the sheath hub 54 is a cantilevered beam, horizontally positioned. When the sheath 1 is retracted, an angled flexible beam 56 attached to the shaft hub 58 (FIG. 18) pops above the surface of the slot 60 and is therefore exposed, as shown in FIGS. 21 and 23. In that case, the end of the angled flexible beam 56 will also be positioned directly under the release button 52. The release button 52 can be activated to push the angled beam 56 below the surface of the slot 60, in which case the spring 14 will push the sheath hub 54 back to its biased extended position, as shown in FIGS. 20 and 22. In addition, a small protrusion is provided on the shaft hub 58, which prevents the sheath 54 from extending any further after the release button 52 is pressed. The protrusion is the sheath hub extension stop.

Figure 25:
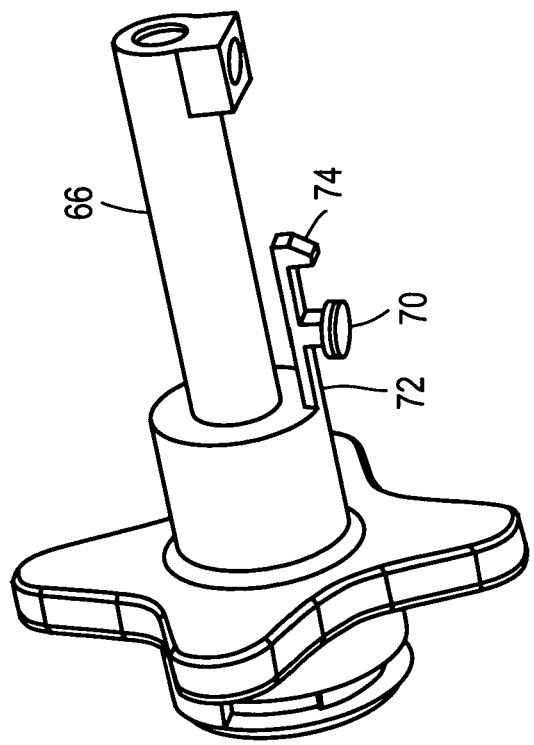
FIG. 25 is a perspective view of the shaft hub according to the second alternative embodiment of the invention.
Figure 24:
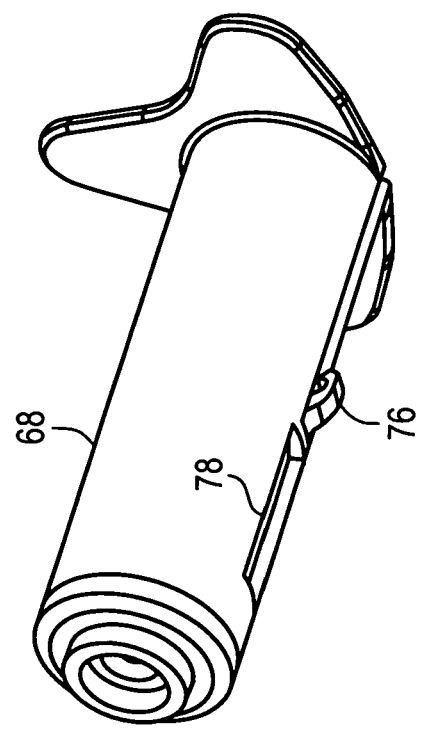
FIG. 24 is a perspective view of the sheath hub according to a second alternative embodiment of the invention.
Figure 26:
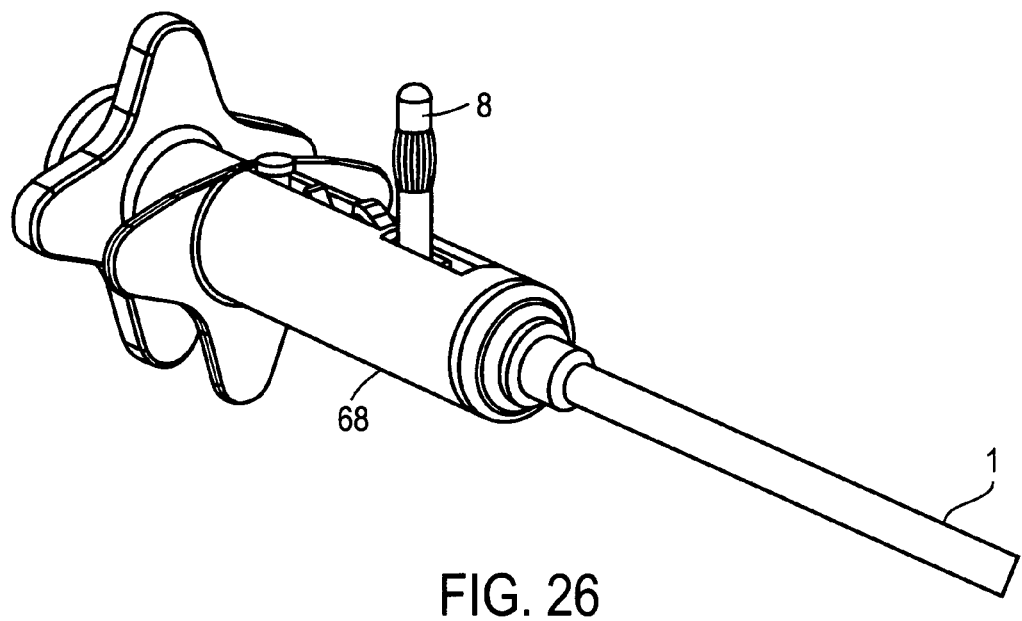
FIG. 26 is a perspective view of the electrosurgical suction/irrigation instrument according to the second alternative embodiment of the invention, with the sheath extended.
Figure 27:
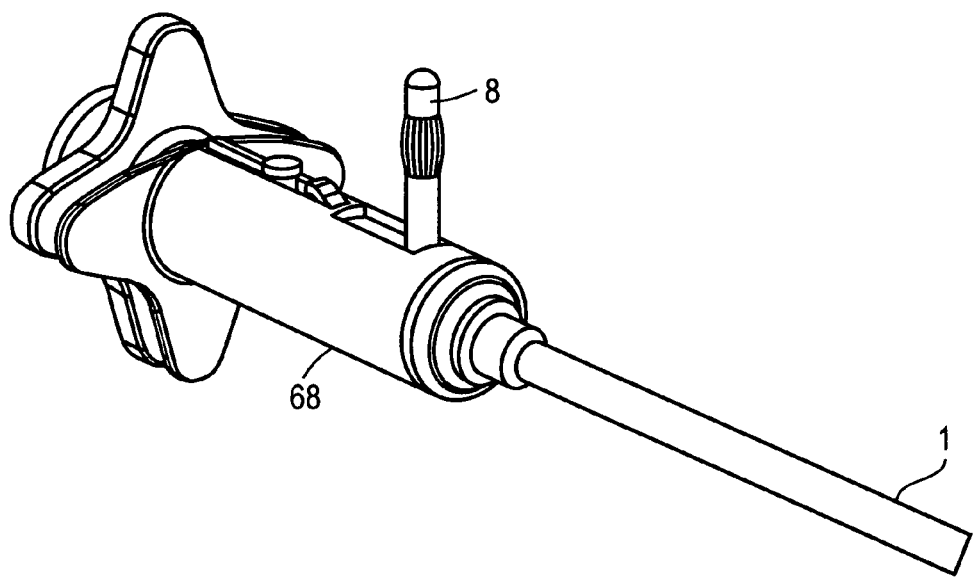
FIG. 27 is a perspective view of the electrosurgical suction/irrigation instrument according to the second alternative embodiment of the invention, with the sheath retracted.

FIGS. 24 through 28 show a second alternative embodiment of the invention. In this embodiment, the locking mechanism is a physical latch. As shown in FIG. 25, the shaft hub 66 has a cantilevered beam 72 with the release button 70 in the middle of the beam 72. The distal end of the beam 72 is the shaft hub latch 74. The sheath hub 68 also has a latch/hook 76, which engages with the shaft hub latch 74 when the sheath 1 is retracted. The release button 70 is pressed to release the shaft hub latch 74 from the sheath hub latch/hook 76. The spring 14 will push the sheath hub 68 back to its biased extended position.

Figure 28:
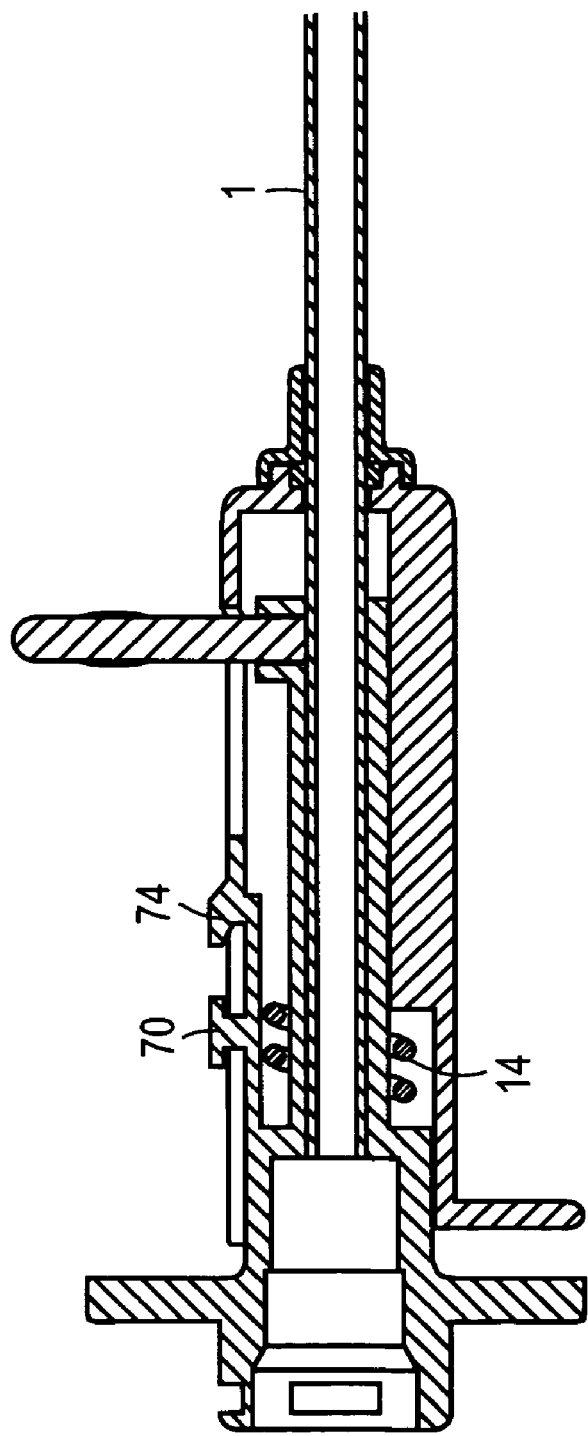
FIG. 28 shows a partial cross-sectional view of the electrosurgical suction/irrigation instrument according to the second alternative embodiment of the invention, with the sheath retracted.

The conductive post 8 is located at the distal end of the shaft hub 66, as shown in FIG. 28. A slot 78 is provided in the sheath hub 68 so that the sheath hub 68 can travel without hitting the conductive post 8. The conductive post 8 acts as a stop that prevents the sheath hub 68 from extending any further after the release button 70 is pressed. Note that the conductive post 8 in this embodiment is located axially in line with the release button 70, in contrast with the previously described embodiments. Note also that once the conductive post 8 is assembled attached to the shaft hub 66, the sheath hub 66 have cannot be removed.

FIGS. 29A through 32 show a third alternative embodiment of the invention. In this embodiment, the locking mechanism is essentially the same as in the embodiment of FIGS. 1 through 17. A latch 82 is provided approximately midway along the flexible beam 84, and when the sheath is fully retracted, the latch 82 pops through the opening 86 in the sheath hub 88 (FIGS. 30A and 30B) and engages with the sheath hub 88. To extend the sheath, the release button 90 is pressed to free the latch 82 from the opening 86. The spring 14 returns the sheath hub 88 back to its biased extended position.

Figure 29A:
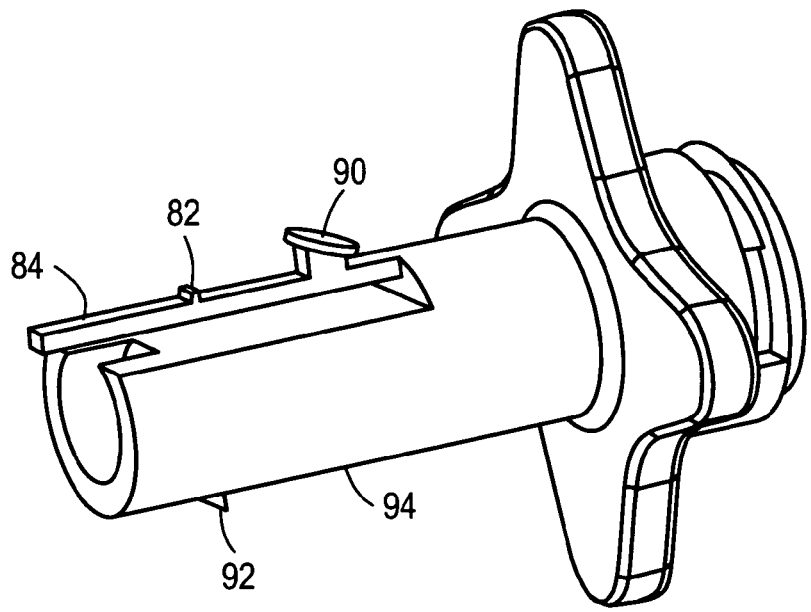
FIGS. 29A and 29B are two perspective views of the shaft hub according to a third alternative embodiment of the invention.
Figure 29B:
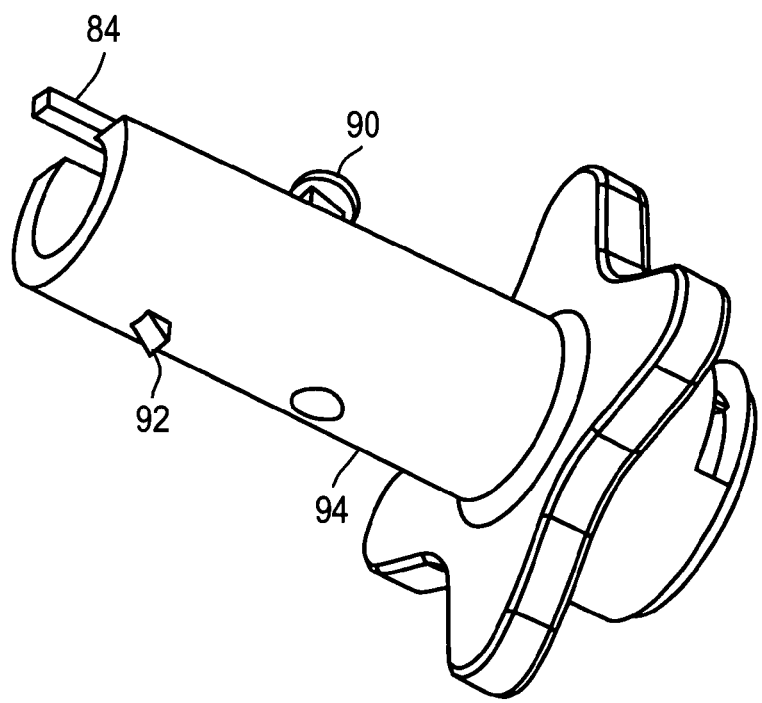
Figure 30A:
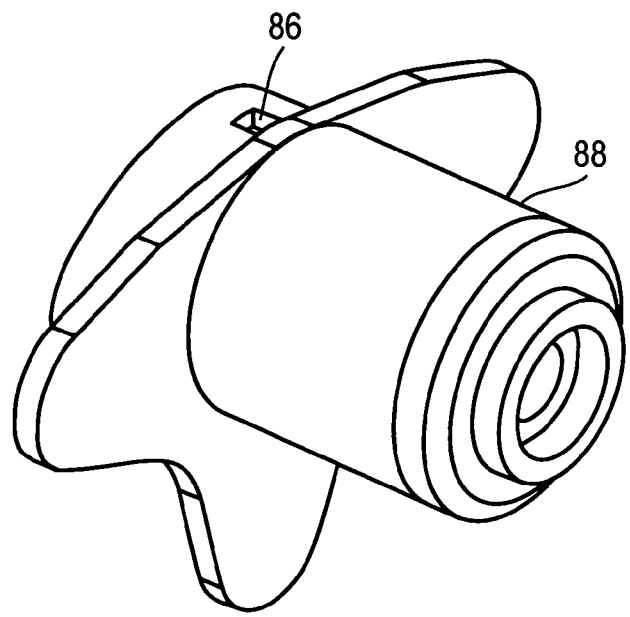
FIGS. 30A and 30B are two perspective views of the sheath hub according to the third alternative embodiment of the invention.
Figure 30B:
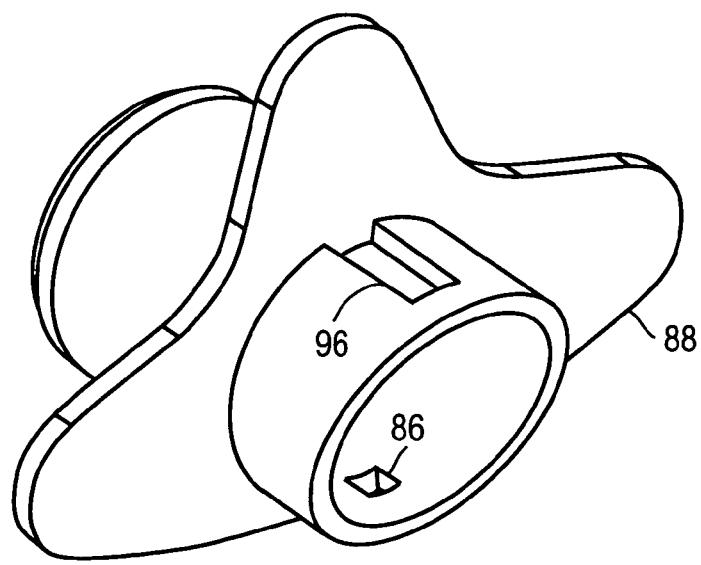
Figure 31A:
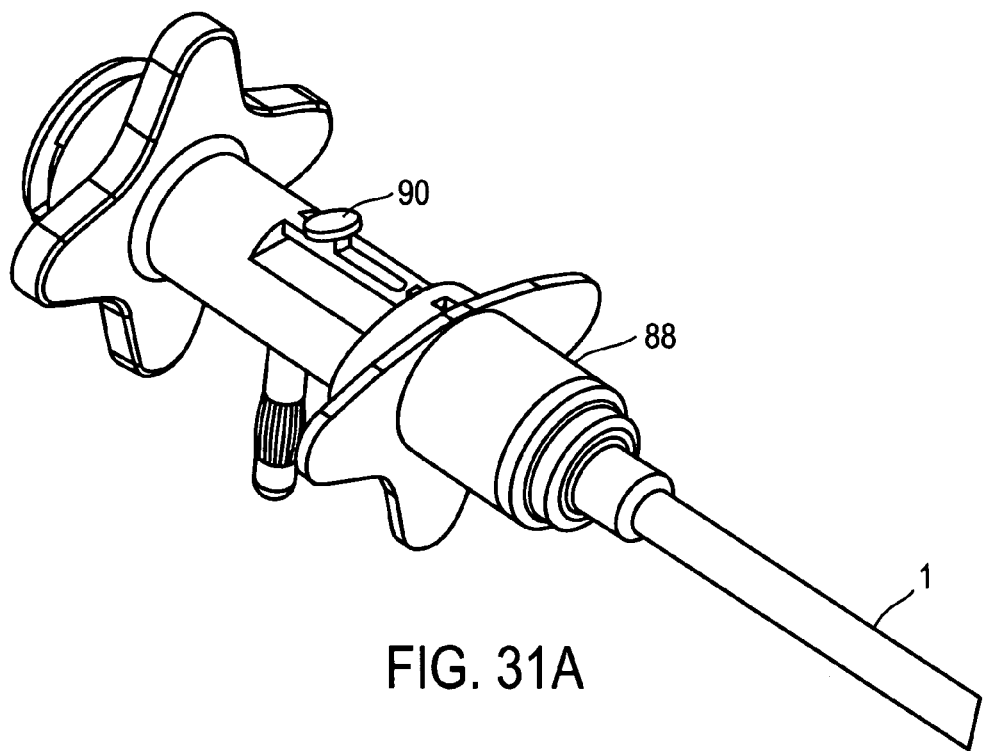
FIG. 31A is a perspective view of the electrosurgical suction/irrigation instrument according to the third alternative embodiment of the invention, with the sheath extended.
Figure 31B:
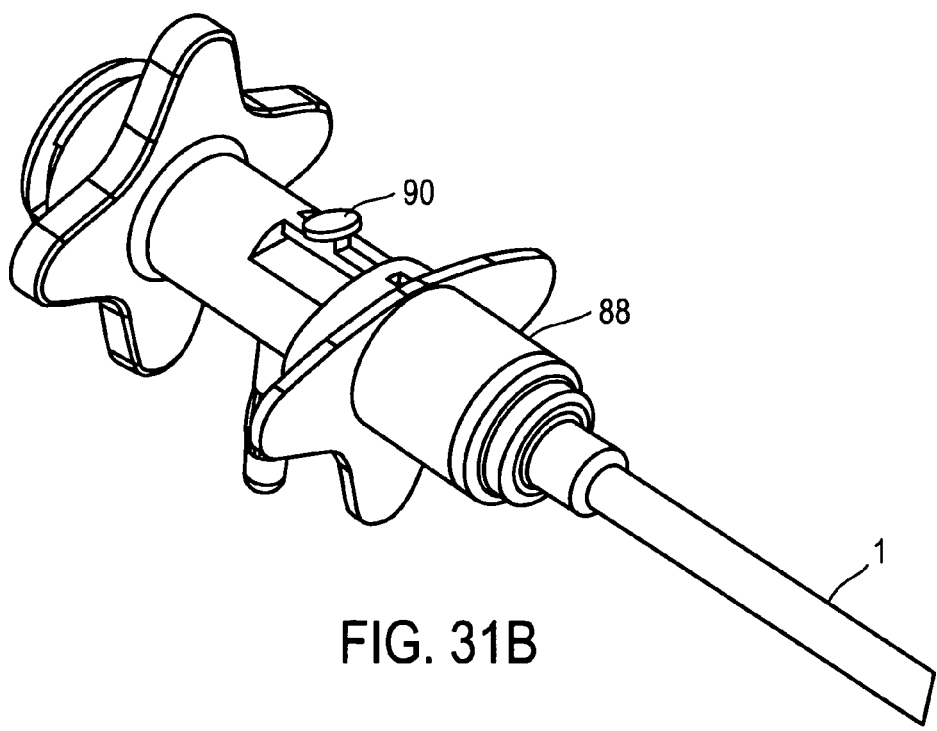
FIG. 31B is a perspective view of the electrosurgical suction/irrigation instrument according to the third alternative embodiment of the invention, with the sheath retracted.
Figure 32:
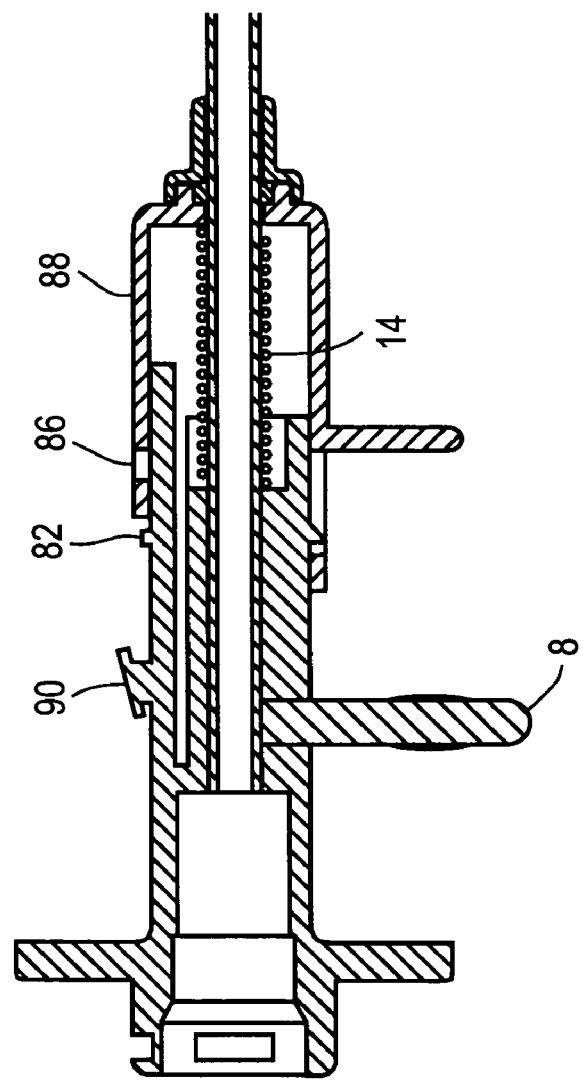
FIG. 32 shows a partial cross-sectional view of the electrosurgical suction/irrigation instrument according to the third alternative embodiment of the invention, with the sheath extended.

A protrusion 92 is provided on the bottom of the shaft hub 94, as shown in FIG. 29B. The protrusion 92 rides along with slot 96 on the bottom of the sheath hub 88 and acts as a stop that prevents the sheath hub 88 from extending any further after the release button 90 is pressed. Note that the conductive post 8 is located more proximally than in the above-described embodiments, and the spring 14 is located more distally, as illustrated in FIG. 32.

Thus, an electrosurgical suction/irrigation instrument with a retractable sheath has been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A surgical instrument comprising:
   a shaft hub;
   an electrically conductive member which has a proximal end mounted to the shaft hub and which has a distal end including a conductive operating tip;
   a sheath to cover the conductive member such that the sheath covers the operating tip when the sheath is in an extended position and the operating tip is exposed when the sheath is in a retracted position;
   a sheath hub coupled to the sheath and movably engaged with the shaft hub;
   a locking mechanism to lock the sheath in the retracted position, the locking mechanism including
      a flexible beam protruding from the shaft hub at an angle, to engage the sheath hub at an opening in the sheath hub while the sheath is in the retracted position, and
      a cantilever beam extending from the sheath hub which, if depressed while the sheath is in the retracted position, repositions the flexible beam to disengage the flexible beam from the opening in the sheath hub; and
   a bias element to bias the sheath toward the extended position.

2. A surgical instrument as recited in claim 1, wherein the shaft hub is removably connectable to a handpiece from which suction and irrigation can be controlled.

3. A surgical instrument as recited in claim 1, wherein the electrically conductive member comprises a tube to channel irrigation solution to an operative site and to channel fluid away from the operative site.

4. A surgical instrument as recited in claim 1, further comprising an electrically conductive post removably mounted to the shaft hub so as to be in electrical contact with the conductive member, the conductive post configured to be coupled to an electrical conductor to receive electrical power from a power source.

5. A surgical instrument as recited in claim 4, wherein the shaft hub comprises a receptacle to receive the conductive post.

6. A surgical instrument as recited in claim 5, wherein the conductive post comprises threading to allow the conductive post to be screwed into the receptacle so that the conductive post is held in contact with the electrically conductive member.

7. A surgical instrument as recited in claim 6, wherein the receptacle comprises no threading prior to an initial mating between the conductive post and the receptacle, and wherein threading is created in the receptacle by the initial mating between the conductive post and the receptacle.

8. A surgical instrument as recited in claim 1, wherein the shaft hub comprises a rotator knob extending radially outward from an outer surface of the shaft hub.

9. A surgical instrument as recited in claim 8, wherein the shaft hub is removably connectable to a handpiece, and wherein the rotator knob allows rotation of the surgical instrument relative to the handpiece when the surgical instrument is coupled to the handpiece.

10. A surgical instrument as recited in claim 9, wherein the sheath hub comprises a retractor flange extending radially outward from an outer surface of the sheath hub to facilitate retraction of the sheath in response to an axial force applied to the retractor flange.

11. A surgical instrument as recited in claim 10, wherein the retractor flange is disposed against the rotator knob when the sheath is in the fully retracted position.

12. A surgical instrument as recited in claim 11, wherein the retractor flange has an outer edge that is at least partially conformal with an outer edge of the rotator knob, such that the retractor flange and the rotator knob form a substantially monolithic shape when the retractor flange is disposed against the rotator knob.

13. A surgical instrument comprising:
   a shaft hub;
   an electrically conductive tube which has a proximal end mounted to the shaft hub and which has a distal end with a conductive operating tip formed thereon;
   a flexible beam protruding from the shaft hub, the flexible beam having an actuator formed thereon, the flexible beam further having a latch formed thereon;
   a retractable tubular sheath covering the conductive tube and which covers the operating tip when the sheath is in an extended position, wherein the operating tip is exposed when the sheath is in a retracted position;
   a sheath hub coupled to the sheath and movably engaged with the shaft hub, the sheath hub including a latch opening which engages the latch when the sheath is retracted, the sheath hub further including a slot through which the actuator extends; and
   a bias element to bias the sheath toward the extended position.

14. A surgical instrument as recited in claim 13, further comprising an electrically conductive post removably mounted to the shaft hub so as to be in electrical contact with the conductive tube, the conductive post configured to be coupled to an electrical conductor to receive electrical power from a power source.

15. A surgical instrument as recited in claim 14, wherein the shaft hub comprises a receptacle to receive the conductive post, and wherein the conductive post comprises threading to allow the conductive post to be screwed into the receptacle so that the conductive post is held in contact with the electrically conductive tube.

16. A surgical instrument as recited in claim 15, wherein the receptacle comprises no threading prior to an initial mating between the conductive post and the receptacle, and wherein threading is created in the receptacle by the initial mating between the conductive post and the receptacle.

17. A surgical instrument as recited in claim 13, wherein the shaft hub comprises a rotator knob extending radially outward from an outer surface of the shaft hub, and wherein the sheath hub comprises a retractor flange extending radially outward from an outer surface of the sheath hub to facilitate retraction of the sheath in response to an axial force applied to the retractor flange.

18. A surgical instrument as recited in claim 17, wherein the retractor flange is disposed against the rotator knob when the sheath is in the fully retracted position.

19. A surgical instrument as recited in claim 18, wherein the retractor flange has an outer edge that is at least partially conformal with an outer edge of the rotator knob, such that the retractor flange and the rotator knob form a substantially monolithic shape when the retractor flange is disposed against the rotator knob.

20. A surgical instrument as recited in claim 13, wherein the bias element comprises a spring disposed around the conductive tube between the sheath hub and the shaft hub.

21. An electrosurgical suction/irrigation instrument comprising:
   a shaft hub that is removably connectable to a handpiece from which suction and irrigation are controlled;
   an electrically conductive tube which has a proximal end mounted to the shaft hub and which has a distal end with a conductive operating tip formed thereon, the electrically conductive tube to channel irrigation solution to an operative site and to channel fluid away from the operative site;

a flexible beam protruding from the shaft hub and extending parallel to the electrically conductive tube, the flexible beam having an actuator and a latch formed thereon;

a retractable tubular sheath covering the conductive tube and which covers the operating tip when the sheath is in an extended position, wherein the operating tip is exposed when the sheath is in a retracted position;

a sheath hub coupled to the sheath and slideably engaged with the shaft hub, the sheath hub including a latch opening which engages the latch when the sheath is retracted to a fully retracted position to lock the sheath in the fully retracted position, the sheath hub further including a slot through which the actuator slideably extends, such that actuating the actuator causes flexing of the flexible beam to disengage the latch from the latch opening to unlock the sheath from the fully retracted position; and a spring disposed around the conductive tube between the sheath hub and the shaft hub to bias the sheath toward the extended position.

22. A electrosurgical suction/irrigation instrument as recited in claim 21, further comprising an electrically conductive post mounted to the shaft hub so as to be in electrical contact with the conductive tube, the conductive post configured to be coupled to an electrical conductor to receive electrical power from a power source.

23. A electrosurgical suction/irrigation instrument as recited in claim 22, wherein the shaft hub comprises a receptacle to receive the conductive post, and wherein the conductive post comprises threading to allow the conductive post to be screwed into the receptacle so that the conductive post is held in contact with the electrically conductive tube.

24. A electrosurgical suction/irrigation instrument as recited in claim 23, wherein the receptacle comprises no threading prior to an initial mating between the conductive post and the receptacle, and wherein threading is created in the receptacle by the initial mating between the conductive post and the receptacle.

25. A electrosurgical suction/irrigation instrument as recited in claim 24, wherein the shaft hub is formed from molded plastic.

26. A electrosurgical suction/irrigation instrument as recited in claim 21, wherein the shaft hub comprises a rotator knob extending radially outward from an outer surface of the shaft hub, and wherein the sheath hub comprises a retractor flange extending radially outward from an outer surface of the sheath hub to facilitate retraction of the sheath in response to an axial force applied to the retractor flange.

27. A electrosurgical suction/irrigation instrument as recited in claim 26, wherein the retractor flange is disposed against the rotator knob when the sheath is in the fully retracted position.

28. A electrosurgical suction/irrigation instrument as recited in claim 27, wherein the retractor flange has an outer edge that is at least partially conformal with an outer edge of the rotator knob, such that the retractor flange and the rotator knob form a substantially monolithic shape when the retractor flange is disposed against the rotator knob.

\* \* \* \* \*